United States Patent [19]
Snell

[11] Patent Number: 5,722,999
[45] Date of Patent: Mar. 3, 1998

[54] SYSTEM AND METHOD FOR STORING AND DISPLAYING HISTORICAL MEDICAL DATA MEASURED BY AN IMPLANTABLE MEDICAL DEVICE

[75] Inventor: Jeffery D. Snell, Oak Park, Calif.

[73] Assignee: Pacesetter, Inc., Sylmar, Calif.

[21] Appl. No.: 510,369

[22] Filed: Aug. 2, 1995

[51] Int. Cl.$^6$ .................................................... A61N 1/02
[52] U.S. Cl. ........................................... 607/32; 607/27
[58] Field of Search ............................. 128/906, 903, 128/904; 62/27, 32

[56] References Cited

U.S. PATENT DOCUMENTS

| | | | |
|---|---|---|---|
| 3,898,984 | 8/1975 | Mandel et al. | 128/2.1 A |
| 4,098,267 | 7/1978 | Stein et al. | 128/2.06 G |
| 4,142,533 | 3/1979 | Brownlee et al. | 128/419 PT |
| 4,281,664 | 8/1981 | Duggan | 128/696 |
| 4,527,567 | 7/1985 | Fischler et al. | 128/419 PT |
| 4,596,255 | 6/1986 | Snell et al. | 128/697 |
| 4,791,936 | 12/1988 | Snell et al. | 128/697 |
| 4,809,697 | 3/1989 | Causey, III et al. | 128/419 PT |
| 4,857,716 | 8/1989 | Gombrich et al. | 128/904 |
| 5,012,411 | 4/1991 | Policastro et al. | 364/413.06 |
| 5,088,488 | 2/1992 | Markowitz et al. | 607/27 |

Primary Examiner—Scott M. Getzow

[57] ABSTRACT

A system and method for acquiring medical data, integrating recently acquired medical data with previously acquired medical data, storing the integrated medical data, and displaying the integrated medical data to a medical practitioner in a convenient format appropriate for the type of data stored are provided. Recently acquired medical data are integrated with historical medical data in an implantable medical device programmer. The data may be initially displayed in graphical and text formats during a patient's follow-up visits. The historical medical data may be stored in the programmer, in the implantable medical device or both. Medical data may include physiologic data pertaining to the patient's medical condition, parametric data pertaining to the operational characteristics of the implantable medical device, identification data, including patient's background information, and comments including the medical practitioner's comments.

56 Claims, 14 Drawing Sheets

SYSTEM AND METHOD FOR STORING AND DISPLAYING HISTORICAL MEDICAL DATA MEASURED BY AN IMPLANTABLE MEDICAL DEVICE

BACKGROUND OF THE INVENTION

This invention relates to implantable medical devices, and in particular to implantable medical devices that are capable of acquiring medical data—including physiologic data pertaining to a patient's medical condition, and parametric data relating to the operational characteristics of the implantable medical device. More particularly, this invention relates to a system and method for acquiring medical data, integrating recently acquired medical data with previously acquired medical data, storing the integrated medical data, and displaying the integrated medical data to a medical practitioner in a convenient format appropriate for the type of data stored.

Some implantable medical devices, such as pacemakers, defibrillators, and cardioverters (collectively referred to as implantable cardiac stimulating devices) are designed to monitor and stimulate the cardiac tissue of patients who suffer from cardiac arrhythmias. Using leads connected to the patient's heart, a cardiac stimulating device typically stimulates cardiac tissue by delivering electrical pulses in response to measured cardiac events which are indicative of a cardiac arrhythmia. Properly administered therapeutic electrical pulses often successfully reestablish or maintain the heart's regular rhythm.

Implantable cardiac stimulating devices can treat a wide range of cardiac arrhythmias by using a series of adjustable parameters to alter the energy content, the shape, the location, and the frequency of the therapeutic pulses. The adjustable parameters are usually defined in a computer program stored in a memory of the implantable device. The program (which is responsible for the operation of the implantable device) can be defined or altered telemetrically by a medical practitioner using an implantable device programmer, such as the one disclosed in the copending, commonly assigned U.S. patent application Ser. No. 08/510,367, filed concurrently herewith, entitled "IMPROVED USER INTERFACE FOR AN IMPLANTABLE MEDICAL DEVICE USING AN INTEGRATED DIGITIZER DISPLAY SCREEN."

Modern implantable medical devices have a great number of adjustable parameters that must be tailored to a particular patient's therapeutic needs. The medical practitioner who implants and configures implantable medical devices is thus faced with a multitude of choices for various implantable medical device settings. An implantable device programmer using a decision support system, such as the one disclosed in the copending commonly assigned U.S. patent application Ser. No. 08/510,365, filed concurrently herewith, entitled "DECISION SUPPORT SYSTEM AND METHOD FOR AN IMPLANTABLE CARDIAC STIMULATING DEVICE," may aid the medical practitioner in configuring the implantable medical device. The disclosed decision support system provides recommendations for implantable device settings depending on the medical practitioner's responses to questions posed by the system.

After initial implantation and configuration of the implantable medical device, the medical practitioner typically performs periodic follow-up examinations to determine if the device is operating properly. On occasion, it may also be desirable for the medical practitioner to alter the device settings to improve the performance of the device. In order to make appropriate decisions regarding such changes, the medical practitioner should consider not only the current condition of the patient and the implantable medical device, but also historical information representative of changes to the patient's condition and changes in the operational characteristics of the implantable medical device.

Historical medical data should be taken into account because, while most implantable medical devices serve patients for years, certain physiologic and parametric changes having an impact on the performance of the device may occur during the time of service. These changes may include changes in characteristics of the patient's cardiac disorder, changes in the patient's course of drug therapy, changes in the patient's overall health, as well as changes in the operational characteristics of the implantable medical device (such as lead impedance and remaining battery life). In addition, medical knowledge about cardiac disorders and preferred methods of treatment may advance during the time of service.

Currently, historical medical data representing changes in the patient's health (i.e., physiologic changes) and changes in the implantable medical device operational characteristics (i.e., parametric changes) are not easily accessible by the medical practitioner. Implantable device programmers have typically presented only the current physiologic and parametric data measurements, while separate computer systems (e.g., dedicated PC database computers, hospital mainframes, etc.) or paper files have served as repositories for historical medical data. Thus, the patient's background information and historical medical data from previous visits may not be immediately available. As a result, the medical practitioner's ability to make more informed decisions regarding settings for the implantable medical device may be impaired since the medical practitioner may not have access to a report which integrates recently acquired medical data with historical medical data during the patient's visit. It is also possible that a medical practitioner may decide not to integrate historical medical data with recently acquired medical data because manual integration of medical data is a difficult and time consuming process. Such a decision is especially likely if the historical medical data is kept in the form of paper files. Thus, a medical practitioner may not discover an important change in the patient's condition or in the operational characteristics of the implantable medical device until well after the patient's visit, when the updated historical medical data report is finally produced.

Moreover, the entry of information into the separate computer and the subsequent production of an updated historical medical data report can be error prone, especially since manual data entry is often used. Even if recently acquired medical data is entered electronically (such as by electronic transfer of a data file containing current physiologic and parametric data from the device programmer to the separate computer), there is a margin of error since the transfer must be manually initiated and the historical medical data report must be manually requested. Furthermore, the operation of an implantable device programmer equipped with a decision support system (as discussed above) is enhanced by the availability of medical data that includes recently acquired and historical medical data, because such data may be useful to the medical practitioner in formulating responses to questions posed by the decision support system.

Another disadvantage of the remote storage of the historical medical data relates to the mobility of the patient. If a patient moves, or has a need to see a medical practitioner about a problem with the implantable medical device while travelling, the historical medical data that resides on the separate computer or paper file that serves as the data repository may not be immediately available to the new examining medical practitioner. Thus, it would be desirable to provide a way for historical medical data to travel with the patient.

In spite of recent advances in implantable device programmer technology, few programmers have progressed beyond the capability of monitoring and displaying recently acquired physiologic and implantable medical device conditions. Even non-programmer physiologic data monitoring systems, such as that disclosed in U.S. Pat. No. 5,012,411 (Policastro et al.) have many limitations. For example, the system of the '411 patent is only capable of monitoring physiologic data and has no capability to interact with an implantable medical device. Furthermore, the device of the '411 patent stores historical medical data in free-form text and has no ability to combine recently acquired and historical medical data, nor does it have any capability for providing up-to-date graphical historical data reports.

In order to significantly improve the follow-up procedure for patients with implantable medical devices, a historical physiologic and parametric data report incorporating recently acquired medical data should be provided in graphical form at the same time that the recently acquired data are reported. The medical practitioner can then make better-informed decisions at the time of the patient's visit. It would also be desirable for the historical medical data report to include the patient's background information and comments made by the medical practitioner during earlier visits in text form.

SUMMARY OF THE INVENTION

In accordance with the present invention, a system and method for acquiring, storing and displaying medical data—including physiologic data pertaining to a patient's medical condition, and parametric data pertaining to the operational characteristics of an implantable medical device—are provided. The system and method of the present invention utilize information processing, storage and display capabilities of an implantable device programmer.

The system of the present invention makes historical physiologic and parametric data, as well as other historical medical data (such as patient background information) available during follow up visits, and also enables the historical data to travel with the patient. Immediate availability of historical medical data provides a solution for the difficulties associated with the unavailability of historical medical data during implantable medical device therapy follow-up visits. Since the system of the present invention also enables historical medical data to travel with the patient, a solution to the problem of a patient being examined by a new medical practitioner in a location different from where the patient's regular follow-up visits occur is addressed as well.

At an initial follow-up visit, the system creates a historical patient data file for containing medical data. The historical patient data file may contain medical data organized in several data formats, including a graphical data format, a textual data format, a form-based data format, and a sampled waveform data format. The medical data in the historical patient data file are updated during subsequent follow-up visits by integrating medical data acquired during each visit with the previously stored historical medical data. As a result, during a follow-up visit, the medical practitioner not only has access to recently acquired medical data (i.e., data acquired during the current visit), but also to the historical medical data collected during earlier visits.

The present invention provides an implantable medical device equipped with data acquisition, data storage, and telemetric communication capabilities, and also provides an implantable device programmer, preferably in form of a portable tablet computer, with data processing, data storage, graphical data display, data output, data communication, telemetric communication, and diagnostic capabilities.

The historical patient data file contains medical data which includes physiologic data, parametric data, identification data, and comments. Physiologic data pertain to the patient's physical condition and may include, but are not limited to, information such as the patient's average heart rate over a period of time, the patient's activity and rate-response histograms, an image of the patient's surface electrocardiogram (ECG), and an image of the patient's intracardiac electrogram (IEGM). Parametric data pertain to the implantable medical device operational characteristics and may include, but are not limited to, information such as remaining battery life and lead impedance of the sensing and pulse-delivering electrodes.

Identification data pertain to both the patient and the implantable medical device. Identification data for the patient may include, but are not limited to, the patient's name, address, information about the patient's attending physician, information about the type and model of implantable medical device, and the patient's course of therapy and course of medication. Identification data for the implantable medical device is typically a unique identifier code (UIC) such as a manufacturer's serial number. Comments may pertain to both the patient and implantable medical device. The comments may include, but are not limited to, annotations linked to physiologic and parametric data, and general comments about the patient's condition or implantable medical device operation.

The present invention advantageously provides several schemes for storing the historical patient data file. For example, the historical patient data file may be stored in the implantable medical device, the implantable device programmer, or both. Each storage scheme has its own particular advantages.

In a first embodiment of the present invention, the historical patient data file is stored in long-term storage memory, such a hard disk drive, located in the implantable device programmer. The implantable device programmer acquires physiologic and parametric data from the implantable medical device through telemetry. The telemetric acquisition of data may also be performed remotely through a data communication pathway (e.g., a telephone line) if the patient with the implantable medical device has access to a remote telemetry device.

The implantable device programmer may also take measurements and perform diagnostic tests by using its internal diagnostic circuitry and by using external equipment other than the implantable medical device. When new medical data are acquired during a follow-up visit, the new medical data may be analyzed, processed, and then integrated with the historical patient data file stored in the programmer storage memory. Text and other information such as the medical practitioner's comments may also be added to the historical patient data file by entering the data into the implantable device programmer through an input device, such as a keyboard or a digitizer pad.

The updated historical patient data file may be graphically displayed, printed, copied to a removable storage medium such as a floppy disk, or transmitted to a separate computer via a suitable communication link.

In a second embodiment of the present invention, the historical patient data file is stored in the implantable medical device memory. In accordance with this embodiment, the implantable medical device memory is preferably split into two memory areas. The first area is used for storing program instructions and the second area is used for storing the historical patient data file and data that may be collected by the implantable medical device between visits. To overcome limitations on the size of implantable medical device memory, the historical patient data file may be compressed. The implantable medical device acquires physiologic data and parametric data during the visit as well as between visits and transmits the recently acquired medical data (including inter-visit data) and the historical patient data file stored in its memory to the implantable device programmer upon request.

The implantable device programmer is used to process, display, print, and optionally compress the historical patient data file and recently acquired medical data received from the implantable medical device. The implantable device programmer may also take measurements and perform diagnostic tests using its internal diagnostic circuitry and using external equipment other than the implantable medical device. Once the recently acquired medical data are integrated with the historical patient data file and are otherwise modified by the medical practitioner, the updated historical patient data file is transmitted from the implantable device programmer to the implantable medical device memory where it is stored until retrieved at the next visit. The updated historical patient data file may also be printed, copied to a removable storage medium such as a floppy disk, or transmitted to a separate computer. Storing the historical patient data file in the implantable medical device memory is advantageous because the historical patient data file travels with the patient and is immediately available to any examining medical practitioner with a compatible programmer.

In a third embodiment of the present invention, the historical patient data file is stored both in the implantable medical device memory and in the implantable device programmer storage memory. Also, to overcome limitations on the size of implantable medical device memory, the historical patient data file may be compressed. The implantable medical device acquires physiologic and parametric data and transmits the recently acquired medical data and the historical patient data file stored in the implantable medical device memory to the implantable device programmer.

The implantable device programmer is used to process, display, store, print and optionally compress the recently acquired medical data and the historical patient data file received from the implantable medical device. The implantable device programmer may also take measurements and perform diagnostic tests using its internal diagnostic circuitry and using external equipment other than the implantable medical device. The implantable device programmer also checks if the historical patient data file received from the implantable medical device is more recent than the historical patient data file stored in its own storage memory. This situation may occur if, for example, the patient misses his regular follow-up visit and is examined by another medical practitioner who modifies the historical patient data file stored in the implantable medical device. The most recent historical patient data file is copied over the older file to ensure that only the most recent historical medical data are retained.

Once the historical patient data file is integrated with recently acquired medical data and is otherwise modified by the medical practitioner, the updated historical patient data file is stored in the programmer storage memory, and is also transmitted from the programmer to the implantable medical device memory.

The updated historical patient data file may also be printed, copied to a removable storage medium such as a floppy disk, or transmitted to a separate computer. Storing the historical patient data file both in the programmer memory and in the implantable medical device memory combines the advantages of the other schemes and also ensures that if either the programmer memory or implantable medical device memory becomes corrupted, the historical patient data file may be recovered from the uncorrupted memory.

The present invention improves the medical practitioner's decision-making ability with regard to determining implantable medical device settings and selecting a course of therapy, by presenting the practitioner with historical medical data in addition to recently acquired medical data which is ordinarily available during follow-up visits. In accordance with the present invention, the medical practitioner can view and analyze trends in patient's condition, patient's responses to particular implantable medical device settings, and trends in implantable medical device operational characteristics over a period of time spanning from the date of device implantation to the present visit.

BRIEF DESCRIPTION OF THE DRAWINGS

The above and other advantages of the invention will be apparent upon consideration of the following detailed description, taken in conjunction with the accompanying drawings, in which like reference numerals refer to like parts throughout, and in which.

DETAILED DESCRIPTION OF THE PREFERRED EMBODIMENTS

Implantable cardiac stimulating devices are commonly used implantable medical devices and will be used to illustrate the principles of the present invention. It should be understood, however, that the principles of the present invention apply equally as well to other types of implantable medical devices, including devices which are intended to monitor a patient's physical condition.

Figure 1:
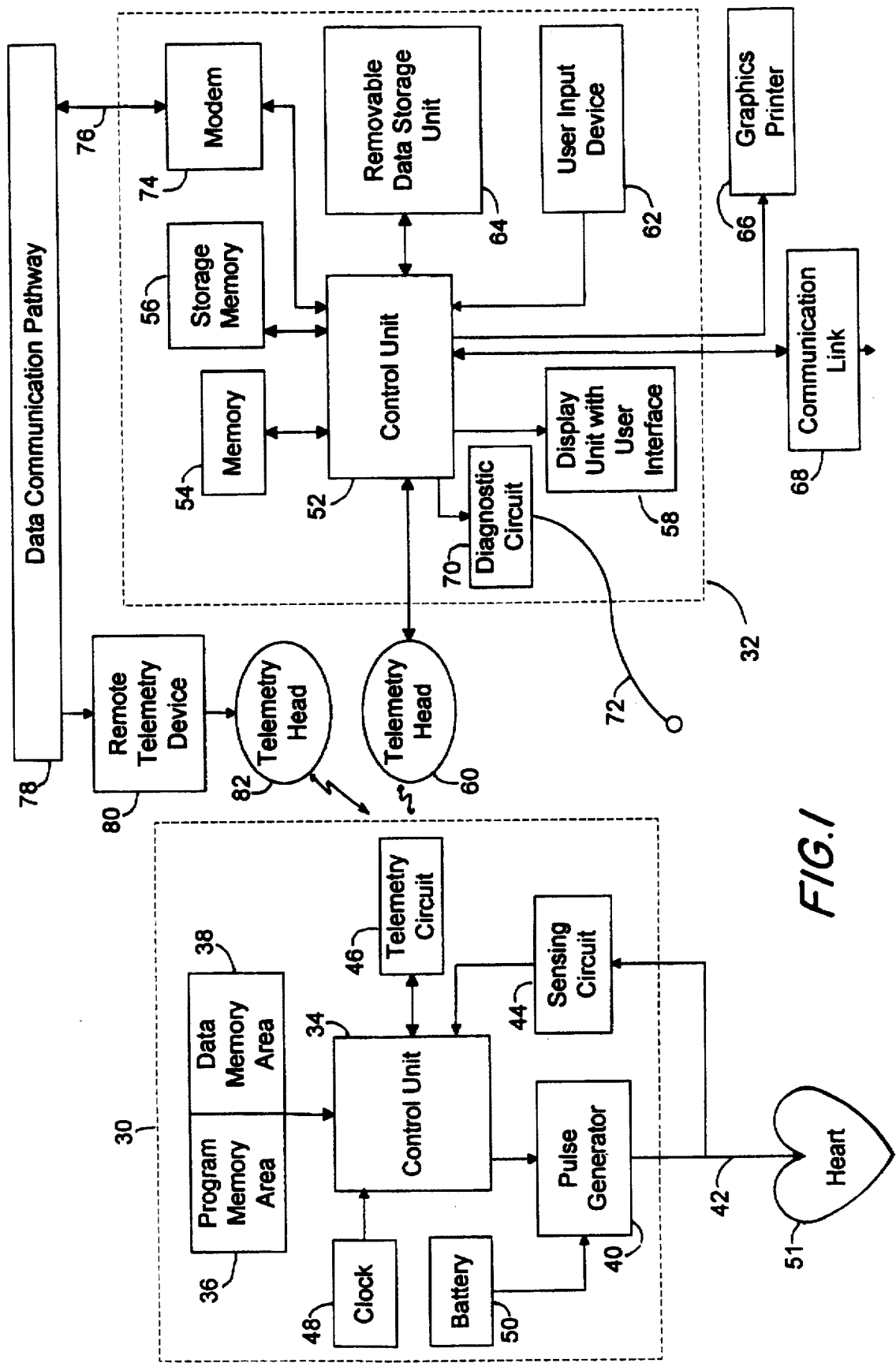
FIG. 1 is a schematic block diagram of a system for acquiring, displaying, and storing a historical patient data file in accordance with the principles of the present invention.

An implantable medical device 30 and an implantable device programmer 32 in accordance with this invention are shown in FIG. 1. The implantable medical device 30 may be a dedicated pacemaker, a cardioverter/defibrillator, or a combination of both. The operation of the implantable medical device 30 is controlled by a control unit 34, which preferably contains control circuitry (not shown) and a microprocessor (not shown) for executing control program instructions that are stored in a program memory area 36. A unique identifier code (UIC), which is preferably a manufacturer's serial number, is also stored in the program memory area 36. The UIC identifies the implantable medical device 30 as a device implanted in a particular patient. A data memory area 38 is provided for storing medical data (i.e., data collected by the implantable medical device 30 between visits). The program memory area 36 and the data memory area 38 may be memory blocks in a single memory unit (shown as a combination of program memory area 36 and the data memory area 38) or may be two separate memory circuits.

The control unit 34 also includes self-diagnostic circuitry (not shown) for monitoring the operational characteristics of the implantable medical device 30, such characteristics including, but not being limited to, battery voltage, battery current, internal battery impedance, and lead impedance. The operational characteristics may be monitored by the implantable medical device 30 between visits. An example of how data pertaining to certain operational characteristics may be acquired between visits is disclosed in the copending commonly assigned U.S. patent application Ser. No. 08/227, 838, filed Apr. 14, 1994, entitled "SYSTEM AND METHOD FOR MEASURING AND STORING PARAMETRIC DATA PERTAINING TO OPERATING CHARACTERISTICS OF AN IMPLANTABLE MEDICAL DEVICE," which is hereby incorporated by reference in its entirety.

A pulse generator 40 is connected to a patient's heart 51 via at least one lead 42. The lead 42 is used for cardiac data acquisition (i.e., sensing the patient's intracardiac electrogram, or IEGM), as well as for delivery of therapeutic pulses. Therapeutic pulses may be pacing pulses delivered to maintain a normal heart rate, or high energy shocks delivered to end an occurrence of a cardiac arrhythmia. The pulse generator 40 generates therapeutic pulses administered through the lead 42 to the patient's heart 51 under direction from the control unit 34. A sensing circuit 44 converts analog data acquired by the lead 42 into digital form which is capable of being analyzed by the control unit 34, stored in the data memory area 38, and transmitted to the programmer 32 by telemetry through an internal telemetry circuit 46. A real time clock 48 is used to provide timing for monitoring cardiac events and for timing the application of therapeutic pulses by the pulse generator 40. A battery 50 supplies the necessary power to the pulse generator 40 (and to other components of the implantable medical device 30 through connections that are not shown).

In one preferred embodiment, the programmer 32 is a pen based tablet computer such as the one disclosed in the above-incorporated U.S. patent application Ser. No. 08/510, 367, entitled "IMPROVED USER INTERFACE FOR AN IMPLANTABLE MEDICAL DEVICE USING AN INTEGRATED DIGITIZER DISPLAY SCREEN." The pen-based tablet computer is advantageous for use in the context of the present invention because of its portability and its graphical user interface with extensive graphical display capabilities. Of course, other computers, especially those capable of displaying graphics, may be used.

As an alternative to conventional telemetry, a modem 74 enables the programmer 32 to communicate telemetrically with the implantable device 30 through a data communication pathway 78 (which may be a typical public telephone line or a cellular link) and a remote telemetry device 80. A data communication link 76 is used to connect the modem 74 to the data communication pathway 78. The data communication link 76 may be a physical connection or a cellular antenna. The remote telemetry device 80 is equipped with a telemetry head 82 for communicating with the implantable medical device 30 through telemetry.

The programmer 32 is controlled by a control unit 52, which is preferably microprocessor-based. A programmer memory 54 (preferably random access memory) is used by the control unit 52 for software operation and data processing, while a storage memory 56 is used for long term data storage. The storage memory 56 may be any type of memory suitable for long term data storage including a hard disk drive, flash memory, or a rewritable optical disk. A table of unique identifier codes (UICs) is stored in the storage memory 56 with each particular UIC entry associated with a corresponding historical patient data file.

The programmer 32 is also provided with a graphical display unit 58. The display unit 58 is used to display recently acquired medical data obtained through the implantable medical device 30, as well as various portions of the historical patient data file such as physiologic and parametric trend graphs, identification data, and comments. An external telemetry head 60 is used to communicate with the implantable medical device 30 through telemetry.

The user interacts with the programmer 32 through a user input device 62, which may be a keyboard, a pen, or even a voice interface. A removable data storage unit 64, such as a floppy disk drive, is also provided for exporting data from the storage memory 56 or the programmer memory 54. One type of data that may be exported is the historical patient data file which the medical practitioner may want to give to a travelling patient, or save as a "back-up" copy, in case the original file becomes corrupted.

An external printer 66 is used to print graphical or textual data at the user's request. An optional communication link 68 may be used to connect to separate computer system, such as a hospital mainframe (not shown) or a dedicated PC database computer (not shown) for transferring data to and from the programmer 32. The communication link 68 may be a physical connection, or a remote connection such as an infrared, a radio frequency, or a cellular link. A diagnostic circuit 70 converts analog surface data acquired by a plurality of external leads 72 into digital form. The digital data may be analyzed by the control unit 52 and stored in the programmer memory 54.

A power source for the programmer 32 may be an on-board battery (not shown) or a power cord (not shown) connected to an electrical power outlet (not shown). The acquisition, processing, display, and storage of medical data are controlled by the programmer 32 through a control program (described below).

A historical patient data file is unique to each particular patient. This file stores medical data of several types such as physiologic data, parametric data, identification data, and comments. Physiologic data pertain to the patient's physical condition and may include, but are not limited to, information such as the patient's average heart rate over a period of time, an image of the patient's intracardiac electrogram (IEGM), and records of various pacing events that may have occurred between visits or during a visit. Physiologic data may be measured by the implantable medical device 30 through the lead 42. In addition to cardiac electrical activity, cardiac mechanical activity may be sensed as described in the copending, commonly assigned U.S. patent application Ser. No. 08/091,636, filed Jul. 14, 1993, entitled "IMPLANTABLE LEADS INCORPORATING CARDIAC WALL ACCELERATION SENSORS AND METHOD OF FABRICATION (as amended)." Physiologic data may also be measured by the programmer 32 through the plurality of external leads 72 (e.g. a surface ECG).

Physiologic data are essential to the medical practitioner because the data show the patient's condition and the effectiveness of implantable medical device therapy. Physiologic data detailing the patient's responses to particular implantable medical device 30 settings may be tracked over several visits. Such data may facilitate the medical practitioner's selection of the settings for the implantable medical device 30 and may therefore affect the entire course of cardiac therapy. Undesirable side effects of implantable medical device therapy may also be ascertained by the medical practitioner when physiologic data are examined.

Parametric data pertain to the operational characteristics of the implantable medical device 30, such as the programmed settings and the results of diagnostic tests that are either performed by the implantable medical device 30 automatically, or that are initiated by the user through the programmer 32. Parametric data may include, but are not limited to, information such as remaining battery life, AV delay, pulse width, pulse energy content (i.e., voltage and current), and lead impedance of the sensing and pulse-delivering leads.

Parametric data are important to the medical practitioner because such data demonstrate the condition and overall performance of the implantable medical device 30 and its internal components over a period of time. For example, by examining parametric data, the medical practitioner may be alerted to a potential problem if the parametric data indicate that the impedance of the lead 42 connecting the implantable medical device 30 to the heart 51 significantly increased since the previous visit. Parametric data also aid the medical practitioner in evaluating the effect of implantable medical device therapy and determining future settings for the implantable medical device 30. The medical practitioner's decision making ability may be further enhanced by evaluating the relationship between the patient's condition (as demonstrated by physiologic data), and the implantable medical device 30 settings (as demonstrated by parametric data).

Identification data may pertain to both the patient and the implantable medical device 30. Identification data for the patient typically include, but are not limited to, the patient's name, address, information about the patient's attending physician, information about the type and model of implantable medical device 30 implanted, information about the patient's course of therapy and any prescribed medications. Identification data for the implantable medical device 30 is typically a unique identifier code (UIC) that is unique to each unit, such as a manufacturer's serial number. Identification data may be important during an emergency, because a medical practitioner who is not the patient's regular attending physician can use the programmer 32 to view information about the patient, about any medications the patient may be taking, about the implantable medical device 30, and about the patient's regular physician—even if the patient is unconscious.

Comments may pertain to both the patient and implantable medical device 30. Comments may include general comments about the patient's condition or the operation of the implantable medical device 30. For example, the medical practitioner might note that the patient complained of severe chest pains when exercising, or that the lead 42 shifted since the last visit. The medical practitioner may also record comments about physiologic or parametric data in form of annotations. Comments are an important type of data, because the medical practitioner may record observations about the patient or the implantable medical device 30 which may not be apparent from other data.

The various types of medical data may be presented in several formats including, but not being limited to, a graphical data format, a textual data format, a form-based data format, and an annotated waveform data format. Graphical data format may include all types of conventional X-Y graphs, histograms, historic vectors, and scatter diagrams. Physiologic data and parametric data may be presented in graphical format. The main advantage of the graphical format is that it allows the medical practitioner to visualize trends in physiologic data and parametric data over a period of time. Examples of physiologic data and parametric data in graphical format are discussed in greater detail below in connection with FIGS. 13–16.

Not surprisingly, identification data and comments are often presented in a textual data format. Information which lends itself to textual presentation may include, but is not limited to, the patient's name and personal information, names, addresses, and telephone numbers of the implanting and follow-up medical practitioners, lists of medications prescribed to the patient, and comments on the condition of the patient and the implantable medical device made during follow-up visits. Comments in form of annotations superimposed over graphs and waveforms may also be presented in the textual data format.

Comments may also be presented in a form-based data format because some comments are often organized in the form of selected answers to multiple choice questions. Multiple choice questions may be posed by the programmer 32 and may relate to diagnostic information describing the indications for implantation of the device, condition and location of the leads, and on-going patient diagnosis. An example of a multiple choice question would be a query as to whether there is evidence of atrial fibrillation, to which the medical practitioner can respond by selecting "yes" or "no."

Parametric data pertaining to the settings of the implantable medical device 30, such as "snap-shot" settings summaries, are also often presented in a form-based data format because determination of the settings may require the medical practitioner to make a selection from several available choices. Form-based acquisition of data is very efficient when the data being acquired are limited to several values, because the medical practitioner is not required to input text. The form-based data format is advantageous for presentation of data containing one or more text fields with multiple choice responses for each field, because of its clarity and organization.

The waveform data format is used for continuous signals that are digitally sampled and then saved in memory as waveforms. The waveforms may be annotated with event markers or other information automatically by the implantable medical device 30, or manually by the medical practitioner using the programmer 32. Certain types of physiologic data, such as the IEGM and ECG waveforms, are presented in the waveform data format. An important characteristic of waveform data is that the data consume a relatively large amount of memory when stored. Physiologic data in the waveform data format are often used by medical practitioners to ascertain the condition of a patient's heart and to detect any cardiac anomalies.

Program instructions and settings for the implantable medical device are stored in the program memory area 36, while the inter-visit data and other data may be stored in the data memory area 38. The relationship between the program memory area 36 and the data memory area 38 may be static or dynamic. In a static relationship, the program memory area 36 and the data memory area 38, may be two different memory circuits. Thus the size of the data memory area 38 for storing historical medical data is fixed and may not be changed.

In a dynamic relationship, the program memory area 36 and the data memory area 38 are memory blocks in a single memory circuit. In a dynamic relationship, the sizes of the program memory area 36 and the data memory area 38 are not fixed but are instead defined by the manufacturer of the implantable medical device 30, and may be adjusted using the programmer 32. Dynamic memory allocation allows the user of the programmer 32 to increase the size of the program memory area 36 to store a more complex control program, thus decreasing the size of the data memory area 38. Dynamic memory allocation also allows the user of the programmer 32 to increase the size of the data memory area 38 allowing a larger amount of data to be stored at the expense of limiting the size of the program memory area 36. Such a dynamic memory allocation scheme is described in the co-pending, commonly assigned U.S. patent application Ser. No. 08/152,999, filed Nov. 12, 1993, entitled "PROGRAMMING SYSTEM HAVING MULTIPLE PROGRAM MODULES," which is hereby incorporated by reference in its entirety.

Figure 2:
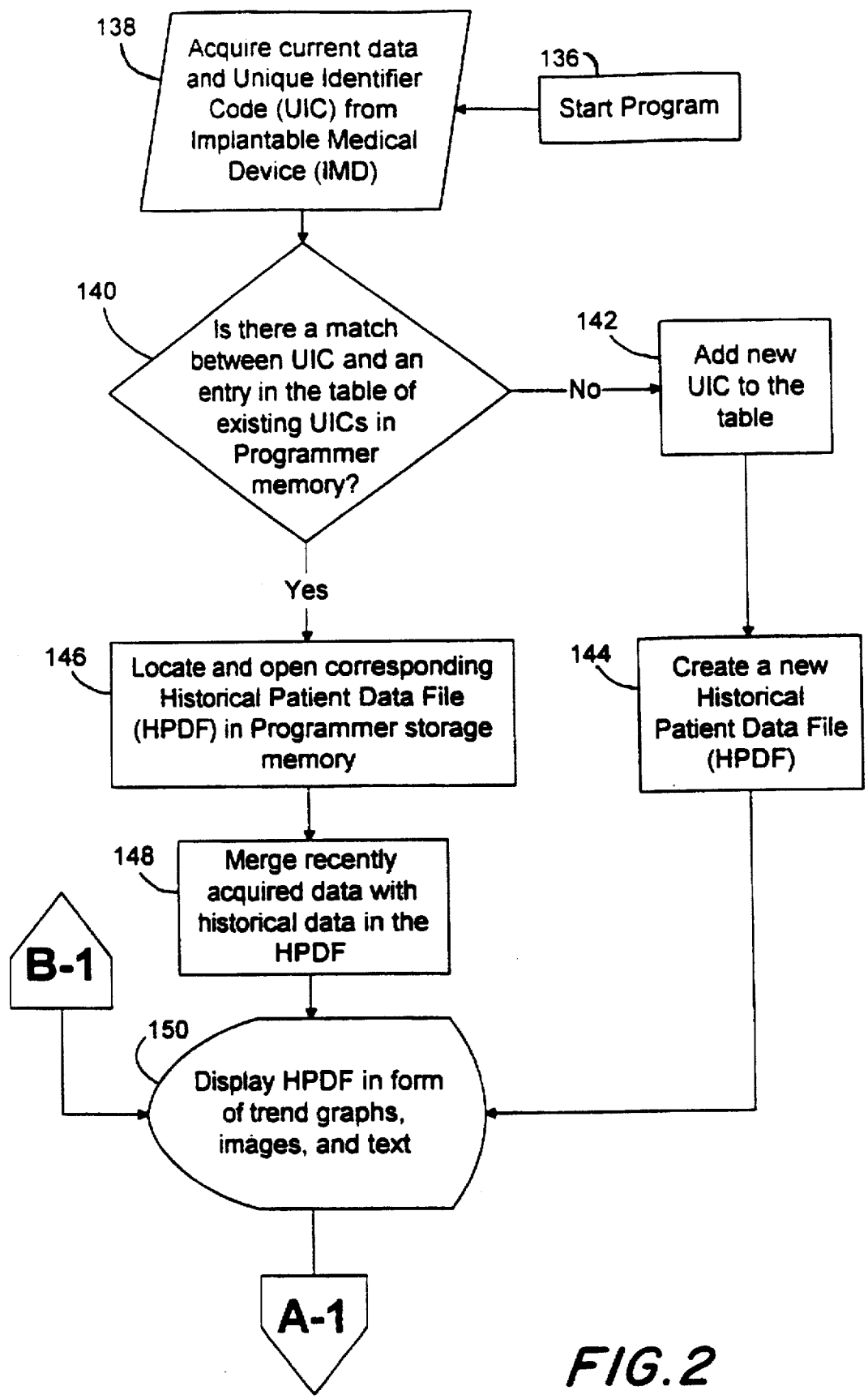
FIGS. 2 and 3 depict a logic flow diagram representative of a control program executed by the implantable device programmer, which is used to direct the operation of a first embodiment of the present invention in which the historical patient data file is stored in the programmer memory in accordance with the principles of the present invention.
Figure 3:
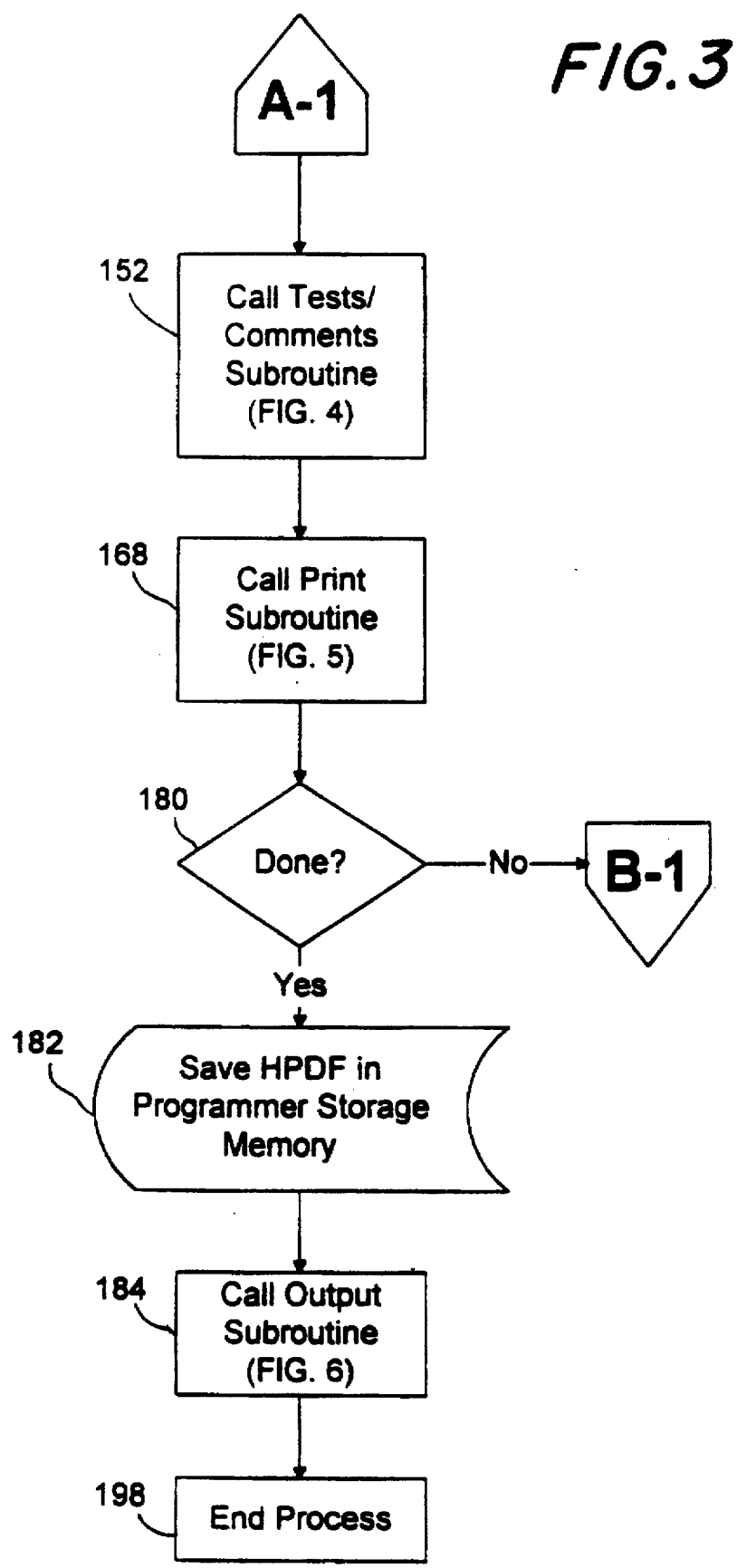

Referring now to FIGS. 2 and 3, a logic flow diagram representing a control program for the control unit 52 of FIG. 1 in accordance with a first embodiment of the present invention is described. In this embodiment, the historical patient data file is stored in the programmer storage memory 56. After the user begins the program at a step 136, the programmer control unit 52 (FIG. 1) acquires medical data from the implantable medical device 30 (FIG. 1) through telemetry at a step 138. The medical data may be acquired through telemetry locally, by using the programmer telemetry head 60 (FIG. 1), or remotely through the data communication pathway 78 (FIG. 1) by using the modem 74 (FIG. 1) and the remote telemetry device 80 (FIG. 1).

Medical data may include, but are not limited to, inter-visit data (if any are present), identification data (e.g., the UIC), and current physiologic and parametric data measured by the implantable medical device control unit 34 (FIG. 1). Physiologic data may include, but are not limited to, the patient's heart rate, event histograms, and IEGM waveforms. Parametric data may include, but are not limited to, self-monitored parametric data generated by the control unit 34 (FIG. 1), which may include battery data such as battery voltage, battery current, battery impedance, atrial and ventricular lead impedances, and implantable medical device 30 settings.

Inter-visit data may be a combination of physiologic and parametric data collected by the implantable medical device 30 between visits. An example of how certain types of parametric data may be acquired between visits is disclosed in the above-incorporated U.S. patent application Ser. No. 08/227,838, filed Apr. 14, 1994. The recently acquired medical data are then temporarily stored in the programmer memory 54 (FIG. 1).

At a test 140, the programmer control unit 52 (FIG. 1) compares the acquired UIC against entries in a table of UICs stored in the storage memory 56 (FIG. 1). This step serves to ascertain whether the particular patient being examined has an existing historical patient data file in the programmer 32 (FIG. 1) by determining whether the UIC acquired from the patient's implantable medical device 30 matches an entry in the table of UICs.

If there is no match, the programmer control unit 52 (FIG. 1) adds the new UIC to the table of UICs at a step 142, and creates a new historical patient data file at a step 144. This file has the capability for storing data in several formats including the graphical data format, the form-based data format, and the waveform data format. The historical patient data file also includes several text fields for containing text-based identification and comments such as the patient's name, type of implantable medical device, date of implantation, attending medical practitioner's name and telephone number, and general comments.

While data in the graphical and waveform data formats may be acquired by the programmer 32 automatically, data in form-based data format are usually entered by the user into a questionnaire form on the programmer display 58. Optionally, to facilitate quick input, the form may contain one or more multiple choice fields which the user may select by simply picking an appropriate choice. This is particularly well suited for questions on the form which may be answered with a "yes" or "no" response. The new historical patient data file also incorporates physiologic and parametric data acquired from the implantable medical device 30 at the step 138. The program then proceeds to a step 150.

However, if at the test 140, the UIC matched an entry in the table of existing UICs, the programmer control unit 52 (FIG. 1) locates the corresponding historical patient data file containing medical data from previous visits in the storage memory 56 (FIG. 1), and loads its contents into the programmer memory 54 (FIG. 1) at a step 146. Of course, if the size of the historical patient data file exceeds memory capacity, the historical patient data file may be loaded in portions or "swapped" from the large capacity storage memory 56 (FIG. 1). The programmer control unit 52 (FIG. 1) then merges the medical data acquired from the implantable medical device 30 (FIG. 1) at the step 138 into the historical patient data file at a step 148. The updated historical patient data file in the programmer memory 54 (FIG. 1) thus integrates medical data acquired during the present visit with medical data acquired during previous visits. Therefore, the user has access to the patient's implantable medical device therapy history during the visit. The program then proceeds to a step 150.

At the step 150 the historical patient data file stored in the programmer memory 54 (FIG. 1) is displayed to the user in form of physiologic and parametric data trend graphs, sampled waveforms, and text fields. Since the viewing area of the graphical display unit 58 (FIG. 1) may be limited, the user may need to move through several screens to view all the information. For example, the first screen may contain all the identification information, such as the patient's background information. The second screen may display physiologic data, while the third screen may display parametric data. The user input device 62 allows the user to navigate through the various screens.

At a step 152, the programmer control unit 52 (FIG. 1) calls a tests/comments subroutine. Subroutines are known in the computer programming art as functions designed to perform specific tasks requested by the main program. One of the advantages of using subroutines is that two or more programs can use the same subroutine to perform a particular function. Modern programming techniques also encompass programmable "objects" which function similarly to subroutines. The main advantage of programmable "objects" is that once an "object" is developed to perform a particular function, it may be used in any program wishing to use that function.

Figure 4:
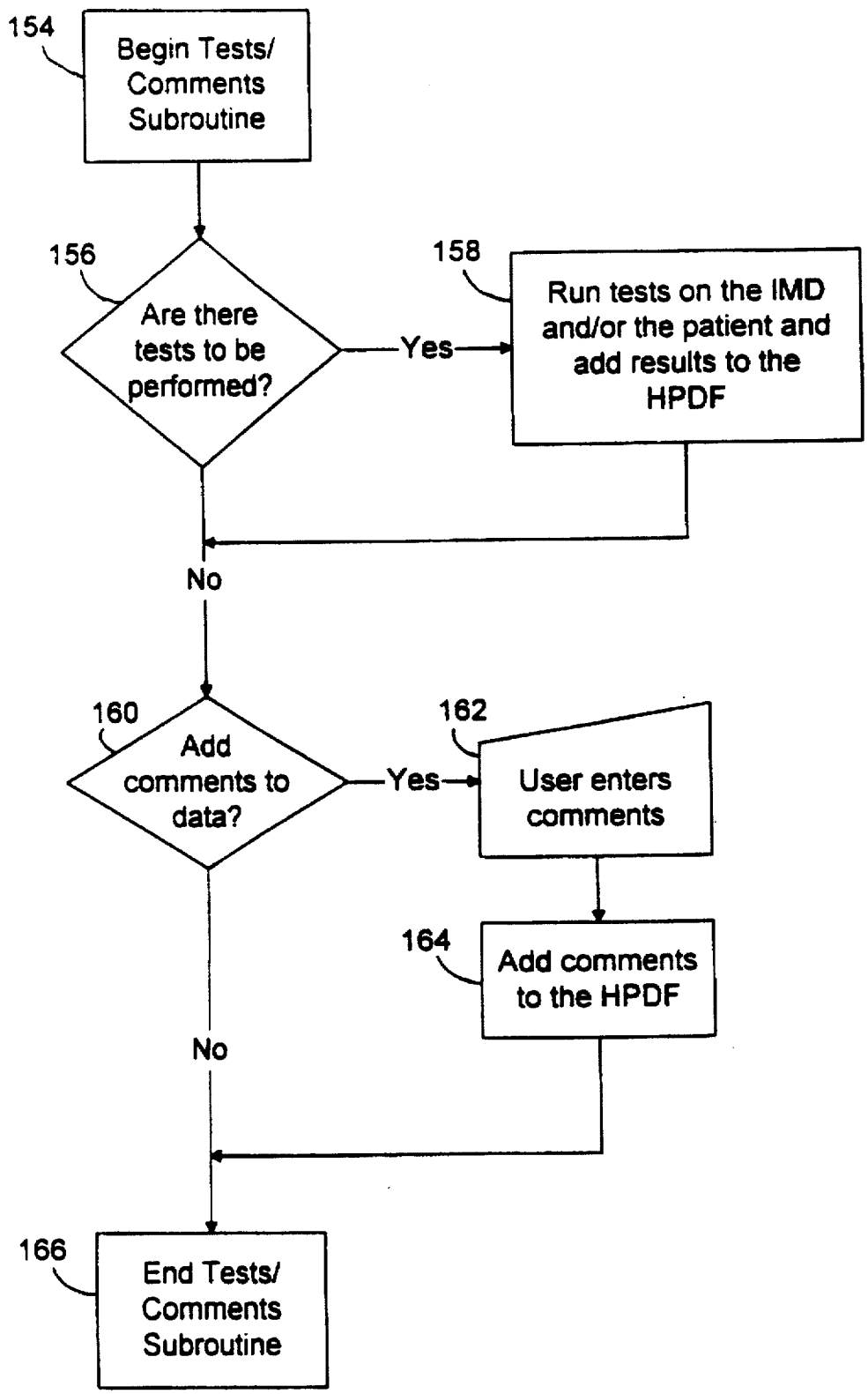
FIG. 4 depicts a logic flow diagram representative of a tests/comments subroutine which allows the user to perform additional tests on the patient or on the implantable medical device, and enables the user to add comments or annotations in text format to the historical patient data file.

The tests/comments subroutine, shown in FIG. 4, allows the user to perform additional tests on the patient or on the implantable medical device 30, and enables the user to add comments such as annotations in text format to the historical patient data file. The tests/comments subroutine begins at a step 154. At a test 156, the programmer control unit 52 (FIG. 1) prompts the user to indicate whether further tests are to be performed. These tests may be typical physiologic data measurements made while the patient is stationary or may involve physiologic data measurements made while the patient is engaged in some form of physical activity prescribed by the medical practitioner, such as running on a treadmill, or breathing heavily.

The tests may also include diagnostic or calibration measurements of the implantable medical device 30 (FIG. 1) that were not performed automatically at the step 138. These tests may include verification of sensor parameter settings or capture threshold tests. The user may also want the programmer 32 to repeat one or more previous physiologic measurements initially made by the implantable medical device 30 (FIG. 1) at the step 138, especially if a measurement appears unusual. If no tests are to be performed, the program proceeds to a test 160. If additional tests are to be performed, at a step 158, the programmer control unit 52 (FIG. 1) runs the requested tests and merges the results of the tests into the historical patient data file. The programmer control unit 52 (FIG. 1) may perform the tests by using the sensing circuit 44 (FIG. 1) through telemetry, by using the diagnostic circuit 70 (FIG. 1), or by using external diagnostic equipment (not shown). The program then proceeds to the test 160.

Whether or not any additional tests are performed, the user is prompted at the test 160 to indicate whether comments are to be added to the historical patient data file. For example, the user may want to record an observation about the patient's condition or provide comments on test results in a textual or form-based format. If no comments are to be added, the program proceeds to a step 166. If comments are to be added, the programmer control unit 52 (FIG. 1) allows the user to input comments at a step 162 through the use of the user input device 62 (FIG. 1). The comments may be added by handwriting the comments on a pen-based tablet computer, by typing the comments on a keyboard, by selecting the comments from a number of presented choices, by recording and digitizing the medical practitioner's speech, or in any combination of the above and other methods. At a step 164, the comments are added to the historical patient data file. The program then proceeds to a step 166. At the step 166, the tests/comments subroutine ends, and control returns to the main program.

Figure 5:
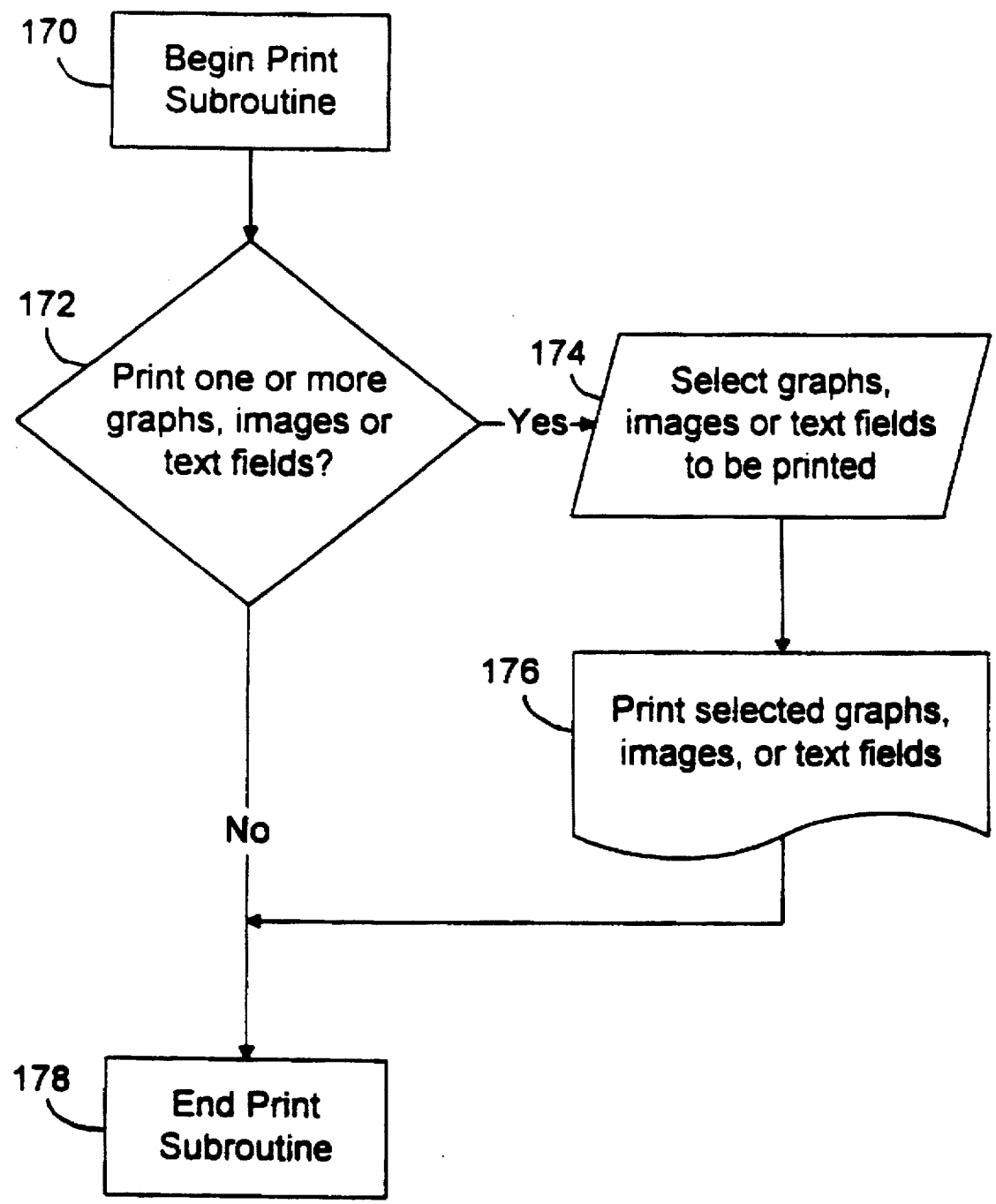
FIG. 5 depicts a logic flow diagram representative of a print subroutine which enables the user to print one or more portions of the historical patient data file.

Returning to FIG. 3, at a step 168, the programmer control unit 52 (FIG. 1) calls a print subroutine. This subroutine, shown in FIG. 5, enables the user to print one or more portions of the historical patient data file stored in the programmer memory 54 (FIG. 1) on the printer 66 (FIG. 1). Referring now to FIG. 5, the print subroutine begins at a step 170. At a test 172, the user is prompted to indicate whether portions of the historical patient data file are to be printed. If no printing is requested, the program proceeds to a step 178. If printing is requested, at a step 174 the user selects either the entire historical patient data file or certain portions of the file, such as physiologic data, parametric data, identification data, and comments, in any combination. For example, if the medical practitioner wishes to examine only parametric data, the practitioner may choose to print only that data. Or, optionally, specific graphs, images or text fields may be selected from various portions of the historical patient data file. This approach gives the medical practitioner the flexibility of printing only the information that is of interest without having to print the entire historical patient data file, which can be quite time consuming. At a step 176, the selected data is printed on the printer 66 (FIG. 1). The program then proceeds to the step 178. At the step 178, the print subroutine ends and control returns to the main program.

Returning now to FIG. 3, at a test 180, the programmer control unit 52 (FIG. 1) queries the user whether the tests/comments and printing procedures are complete. If the procedures are not complete, the programmer control unit 52 (FIG. 1) returns to the step 150 where the updated historical patient data file is displayed. The user may then run more tests, and add more comments. If the procedures are complete, at a step 182, the updated historical patient data file stored in the programmer memory 54 (FIG. 1) is saved to the storage memory 56 (FIG. 1) for long-term storage. The programmer control unit 52 (FIG. 1) then calls an output subroutine at a step 184.

Figure 6:
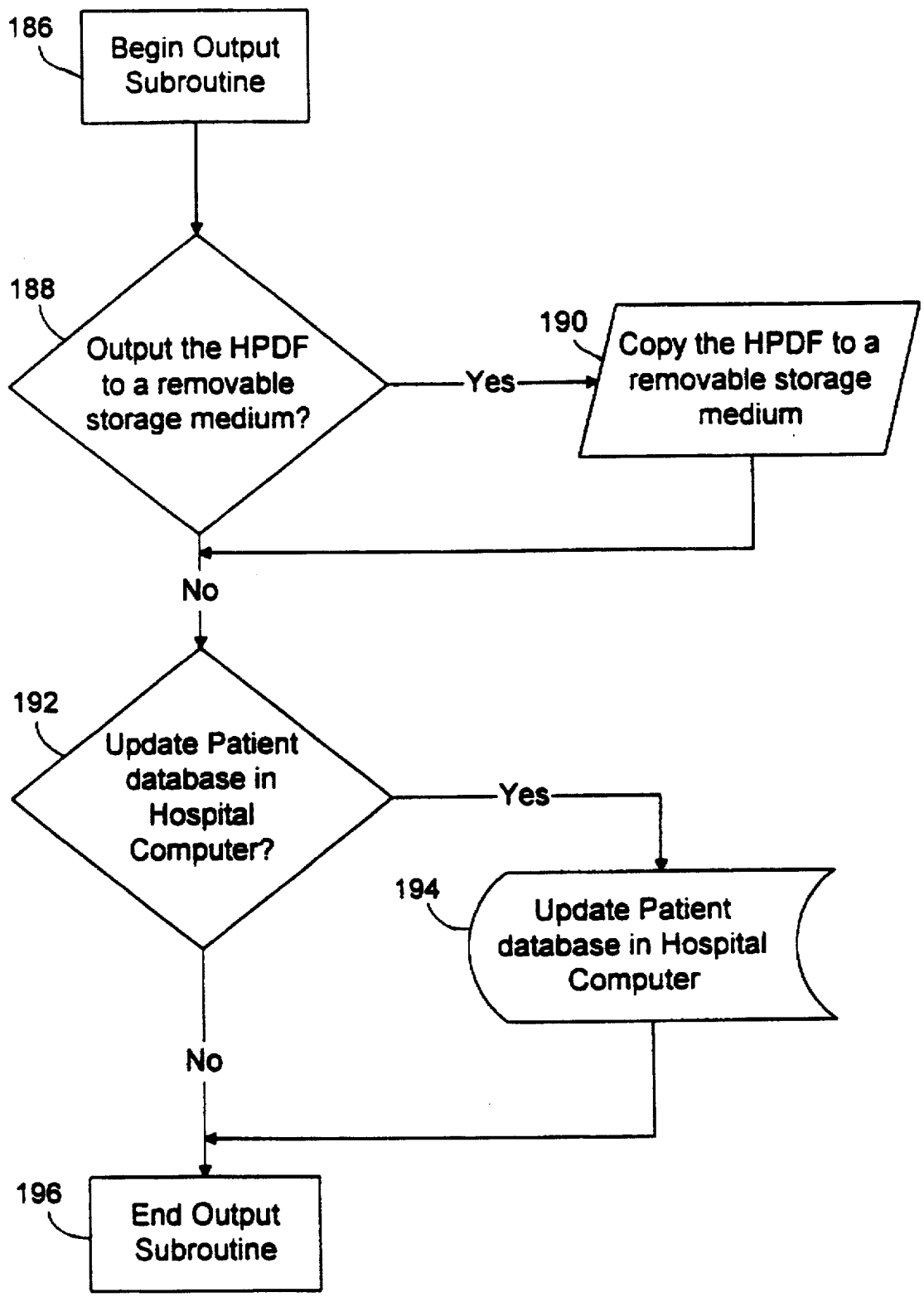
FIG. 6 depicts a logic flow diagram representative of an output subroutine which enables the user to copy the historical patient data file to a removable storage medium and to update a separate computer system.

Referring now to FIG. 6, the output subroutine, which begins at a step 186, provides the user with several output options. At a test 188, the user is asked whether the historical patient data file should be copied to a removable storage medium (such as a floppy disk) at the removable storage unit 64 (FIG. 1). If no copying is requested the program proceeds to a test 192. If copying is requested, the programmer control unit 52 (FIG. 1) copies the historical patient data file to a removable storage medium at a step 190. This feature allows the patient to carry medical data from previous visits on the removable storage medium. This is especially important if the patient experiences a cardiac disorder while travelling. By using the removable storage medium (such as a floppy disk), a medical practitioner with a compatible programmer can access the patient's implantable medical device treatment history, which greatly aids in providing any necessary treatment. The program the proceeds to the test 192.

At the test 192, the programmer control unit 52 (FIG. 1) prompts the user to indicate whether the separate computer (not shown) which commonly stores historical patient information should be updated with medical data acquired during the current visit. If the separate computer is not to be updated, the program proceeds to a step 196. If the separate computer is to be updated, at a step 194, the programmer control unit 52 (FIG. 1) copies the historical patient data file from the programmer memory 54 to the corresponding separate computer patient information file via the communication link 68 (FIG. 1). The program then proceeds to the step 196. At the step 196 the output subroutine ends and control returns to the main program.

Returning to FIG. 3, at a step 198, the programmer control unit 52 (FIG. 1) ends the program and returns to an initial display screen (not shown) on the display unit 58 (FIG. 1) where the user may begin another program.

In a second embodiment of the present invention, the historical patient data file is stored in the implantable medical device data memory area 38 (FIG. 1). While it may be advantageous to use the superior processing power of the programmer 32 to manage the various forms of medical data, storing the historical patient data file in the data memory area 38 provides certain advantages over storing the file only in the programmer storage memory 56. The main advantage is that the patient is provided with the most recent medical data stored in the memory area 38 (FIG. 1), which may be accessed by any medical practitioner with a compatible programmer. Unlike the previously described embodiment, no floppy disk needs to be carried by the patient, although the medical practitioner may still provide one.

Figure 7:
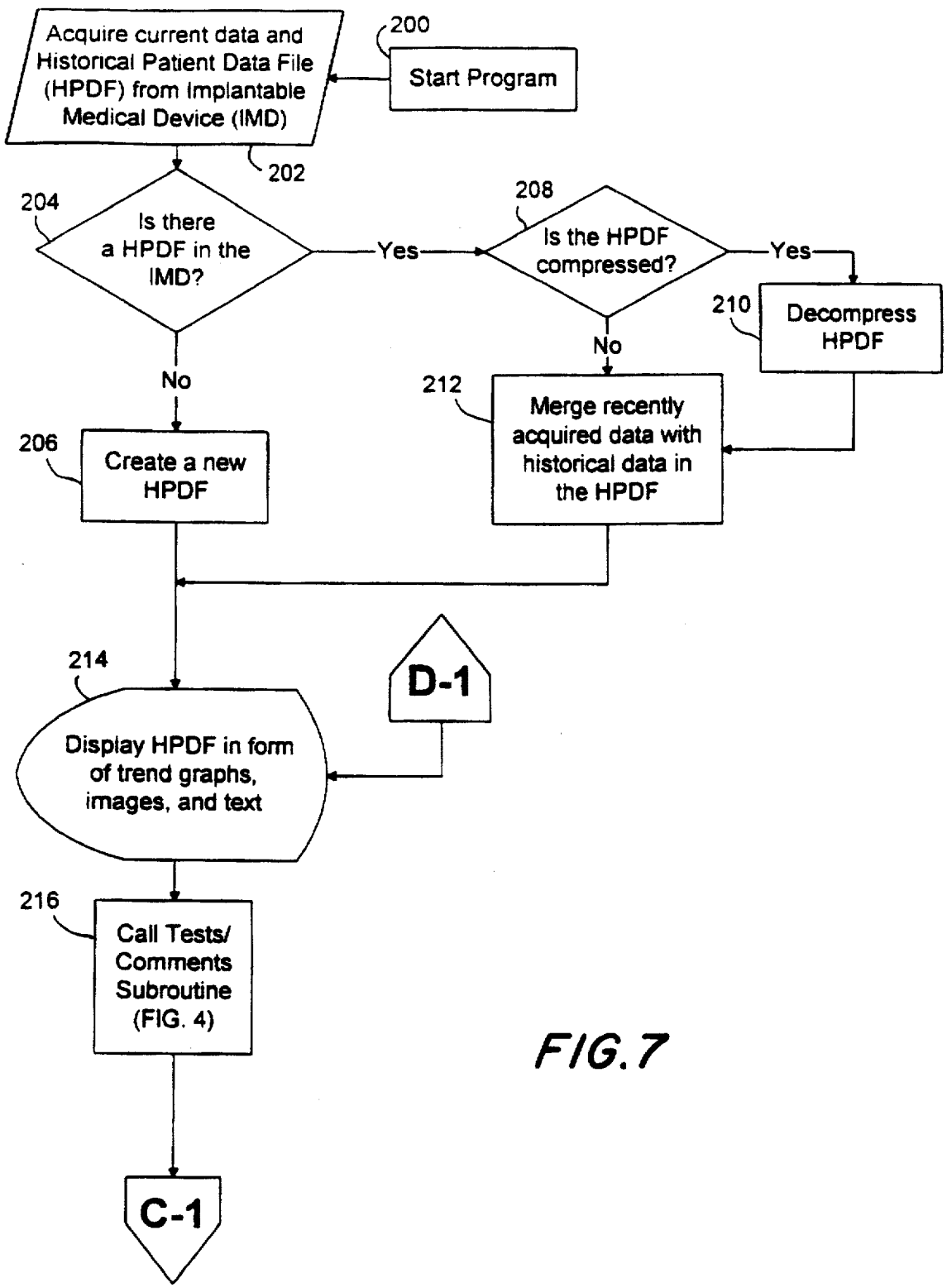
FIGS. 7 and 8 depict a logic flow diagram representative of a control program executed by the implantable device programmer, which is used to direct the operation of a second embodiment of the present invention in which the historical patient data file is stored in the implantable medical device memory.
Figure 8:
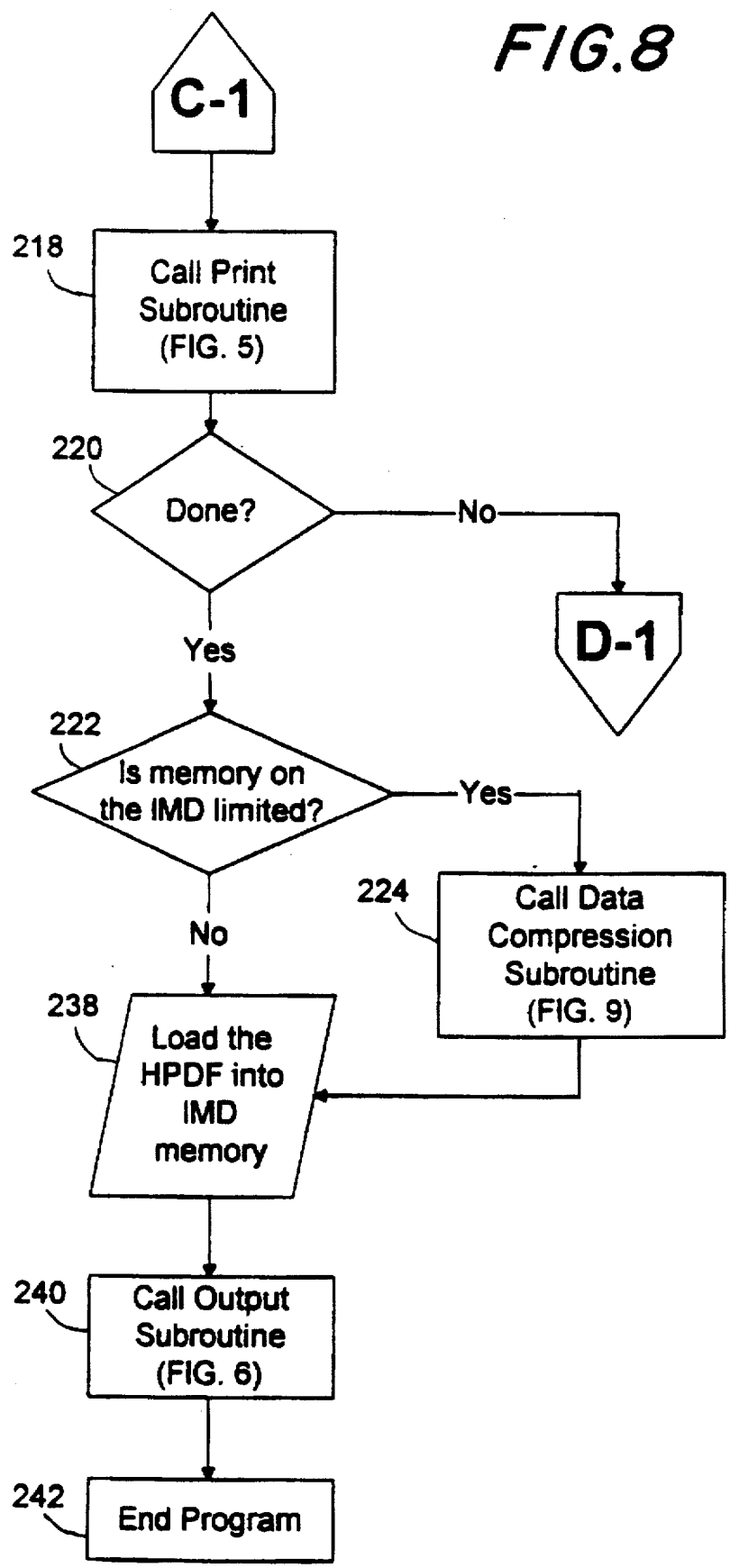

Referring now to FIGS. 7 and 8, a logic flow diagram representing a control program for the control unit 52 of FIG. 1 in accordance with a second embodiment of the present invention is described. The user begins the program at a step 200. At a step 202, the programmer control unit 52 (FIG. 1) acquires medical data from the implantable medical device 30 (FIG. 1) through telemetry. Medical data may include, but are not limited to, inter-visit data (if any are present), identification data (e.g., the UIC), and current physiologic and parametric data measured by the implantable medical device 30 (FIG. 1). At the step 202, the programmer control unit 52 (FIG. 1) also acquires the contents of the data memory area 38 (FIG. 1), where a historical patient data file may be stored. The medical data and historical patient data file acquired at the step 202, may be acquired through telemetry locally, by using the programmer telemetry head 60 (FIG. 1), or remotely through the data communication pathway 78 (FIG. 1) by using the modem 74 (FIG. 1) and the remote telemetry device 80 (FIG. 1). The recently acquired medical data and the historical patient data file are then temporarily stored in the programmer memory 54 (FIG. 1).

At a test 204, the programmer control unit 52 (FIG. 1) determines whether a historical patient data file was acquired from the data memory area 38 (FIG. 1) at the step 202. If a historical patient data file was not acquired, this is most likely the patient's first visit with the examining medical practitioner. Thus at a step 206, a new historical patient data file is created in the programmer memory 54 (FIG. 1). The new historical patient data file also incorporates the recently acquired medical data received from the implantable medical device 30 at the step 202.

If at the test 204, a historical patient data file was acquired from the data memory area 38 (FIG. 1), at a test 208, the programmer control unit 52 (FIG. 1) checks whether the historical patient data file is compressed. If the historical patient data file is not compressed, the program proceeds to a step 212. If the file is compressed, the programmer control unit 52 (FIG. 1) decompresses the historical patient data file at a step 210 and loads the file into the programmer memory 54 (FIG. 1). Data decompression methods depend on the type of data involved and the type of compression algorithm used. For example, algorithms that are used for compressing image data are quite different from binary text compression algorithms. Different types of compression algorithms are further discussed in the description of the compression subroutine described below in connection with FIG. 9. The program then proceeds to a step 212. At the step 212, the programmer control unit 52 (FIG. 1) merges the medical data acquired at the step 202, into the decompressed historical patient data file.

At a step 214, the historical patient data file stored in the programmer memory 54 (FIG. 1) is displayed to the user in form of physiologic and parametric data trend graphs, sampled waveforms, and text fields. At a step 216, the programmer control unit 52 (FIG. 1) calls the tests/comments subroutine (described above in connection with FIG. 4), which allows the user to perform additional tests on the patient and the implantable medical device 30 and add comments and test results to the historical patient data file. At a step 218, the programmer control unit 52 (FIG. 1) calls the print subroutine (described above in connection with FIG. 5). The print subroutine enables the user to print one or more portions of the historical patient data file stored in the programmer memory 54 (FIG. 1) on the printer 66 (FIG. 1).

At a test 220, the programmer control unit 52 (FIG. 1) queries the user as to whether the tests/comments and printing procedures are complete. If the procedures are not complete, the programmer control unit 52 (FIG. 1) returns to the step 214 where the updated historical patient data file is displayed. The user may then run more tests and add more comments. If the procedures are complete, at a test 222 the programmer control unit 52 (FIG. 1) checks if the data memory area 38 (FIG. 1) is of sufficient size to accommodate the storage of the decompressed historical patient data file. If the data memory area 38 (FIG. 1) is of sufficient size, the program proceeds to a step 228. If the data memory area 38 (FIG. 1) is of insufficient size, the programmer control unit 52 (FIG. 1) calls a compression subroutine at a step 224.

Figure 9:
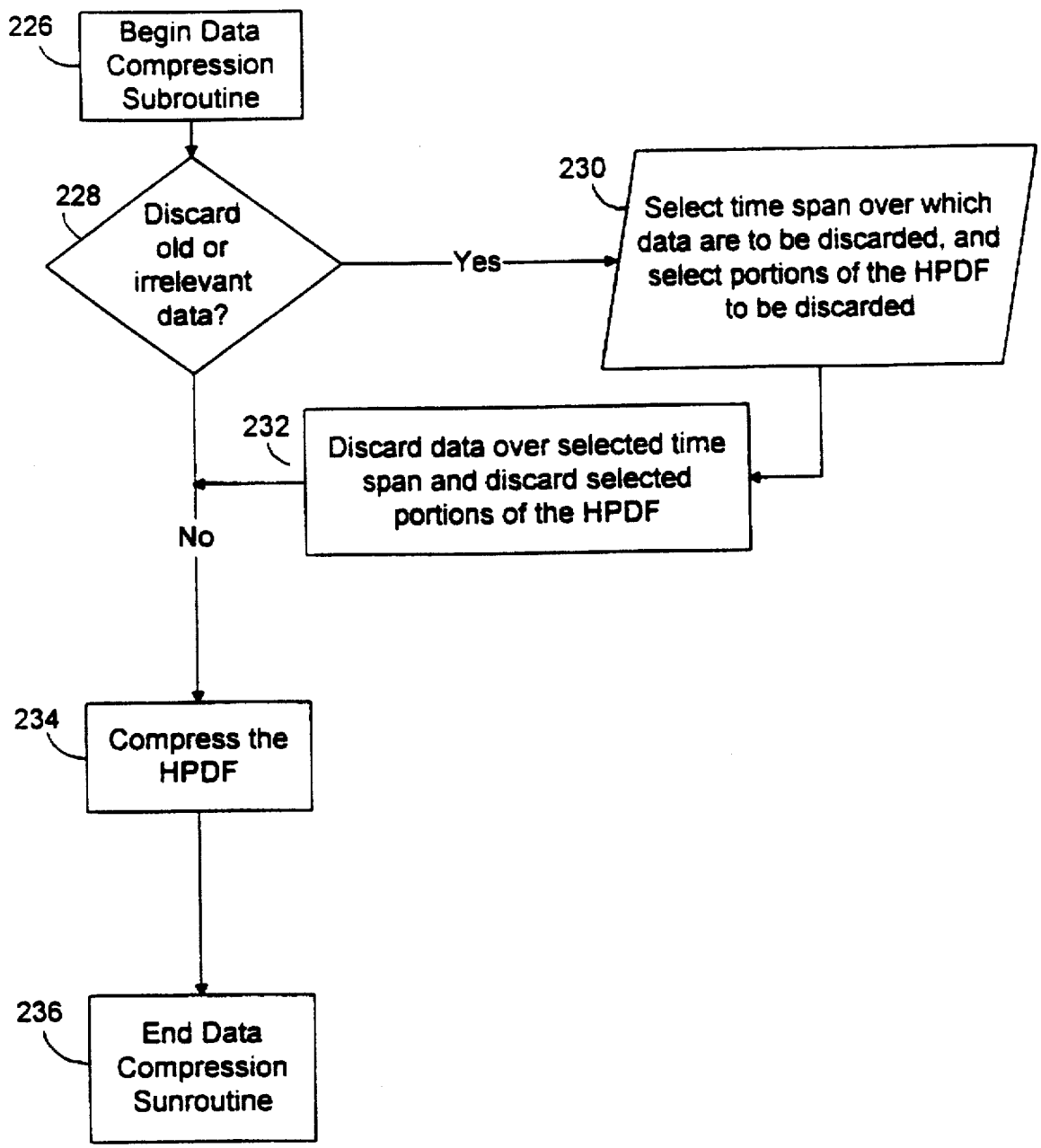
FIG. 9 depicts a logic flow diagram representative of a data compression subroutine which enables the programmer to compress the historical patient data file for storage in the implantable medical device memory.

The compression subroutine shown in FIG. 9 allows the data memory area 38 (FIG. 1) to store a much greater amount of data than would otherwise be possible. The compression subroutine begins at a step 226. At a test 228, the user is prompted whether old medical data should be discarded. For example, if the values of certain parameters have not changed over a long period of time, the user may wish to delete the older information. Also, if due to the pattern of therapy, certain portions of the historical patient data file are no longer important, the user may want to delete the irrelevant portions to reduce the size of the historical patient data file. If no data are to be discarded, the program proceeds to a step 234.

If some data are to be discarded, at a step 230, the user selects the time span over which the data should be discarded. For example, if the patient has the implantable medical device 30 for three years, the user may want to delete some physiologic or parametric data from the first two years after implantation. At the step 230, the user may also select which portions of the historical patient data file (if any) are to be deleted entirely. For example, the medical practitioner may no longer be interested in the patient's R-wave amplitude, and may want to remove the R-wave amplitude information from the historical patient data file. At a step 232, portions of the historical patient data file selected at the step 230 are deleted over the selected time span, along with entire portions of the historical patient data file, if any were selected at the step 230. The program then proceeds to the step 234.

At the step 234 the subroutine compresses the historical patient data file, using compression algorithms appropriate to each data format. In the art of data compression, it is known that compression methods generally rely on the presence of redundant information in the input data. The compression methods are constructed based on a model of the expected input data, such as text data, sampled waveform data, and form-based data. The efficiency of a compression method is directly proportional to the quality of the model the method was based on. Many of the compression algorithms that are in use today are designed to compress random text or program code. Thus, most expected input data models are based on random natural language text. Examples of random natural text compression include Huffman's method, Lempel-Ziv compression, and Katajainen's syntax directed compression method. Other compression methods exist for data types other than text or program code.

Data in the graphical data format, which consist of relatively fixed set of distinct parameters with a finite number of possible values, are best compressed by storing the individual values as packed bit fields. Data from the historical patient data file in the textual data format is usually small in size and thus little redundant information is present. As a result, standard random natural text compression would not be efficient. Thus, the preferred compression technique for the historical patient data file text is a form of bit field packing that allows the encoding of text characters.

Data in the form-based data format lends itself to compression easily. Since the form itself is fixed, each field in the form needs just enough bits assigned to it to code the possible number of choices for that field. The bit packing compression method is preferable for the form-based data as well.

Compression of data in the waveform data format is generally based on a continuous waveform model. Examples of waveform compression techniques include differential pulse code modulation and entropy coding, AZTEC, Turning-point, and CORTES. Furthermore, since a waveform contains a relatively large amount of redundant information, a compression model in which some data are discarded may be acceptable. The waveform data stored in the patient data file may be compressed using any of the suitable continuous waveform compression methods.

When data needs to be decompressed at some future point, the main program has the capability of identifying the compression method used on each data format and reversing the procedure to decompress the data. The identification may be made through use of a file header which identifies the compression method or methods used. After data compression is complete, the compression subroutine ends at a step 236, and control returns to the main program.

Returning now to FIG. 8, the programmer control unit 52 (FIG. 1) then loads the updated and compressed historical patient data file into the data memory area 38 (FIG. 1) at a step 238. The historical patient data file may be loaded into the data memory area 38 (FIG. 1) through telemetry locally, by using the programmer telemetry head 60 (FIG. 1), or remotely through the data communication pathway 78 (FIG. 1) by using the modem 74 (FIG. 1) and the remote telemetry device 80 (FIG. 1). The program then proceeds to the step 240. At the step 242 the programmer control unit 52 (FIG. 1) calls the output subroutine (described above in connection with FIG. 6), which allows the user to output the updated historical patient data file to a removable storage medium and to update the separate computer system. The program ends at a step 242, and returns to the initial display screen (not shown) on the display unit 58 (FIG. 1) where the user may begin another program.

Figure 10:
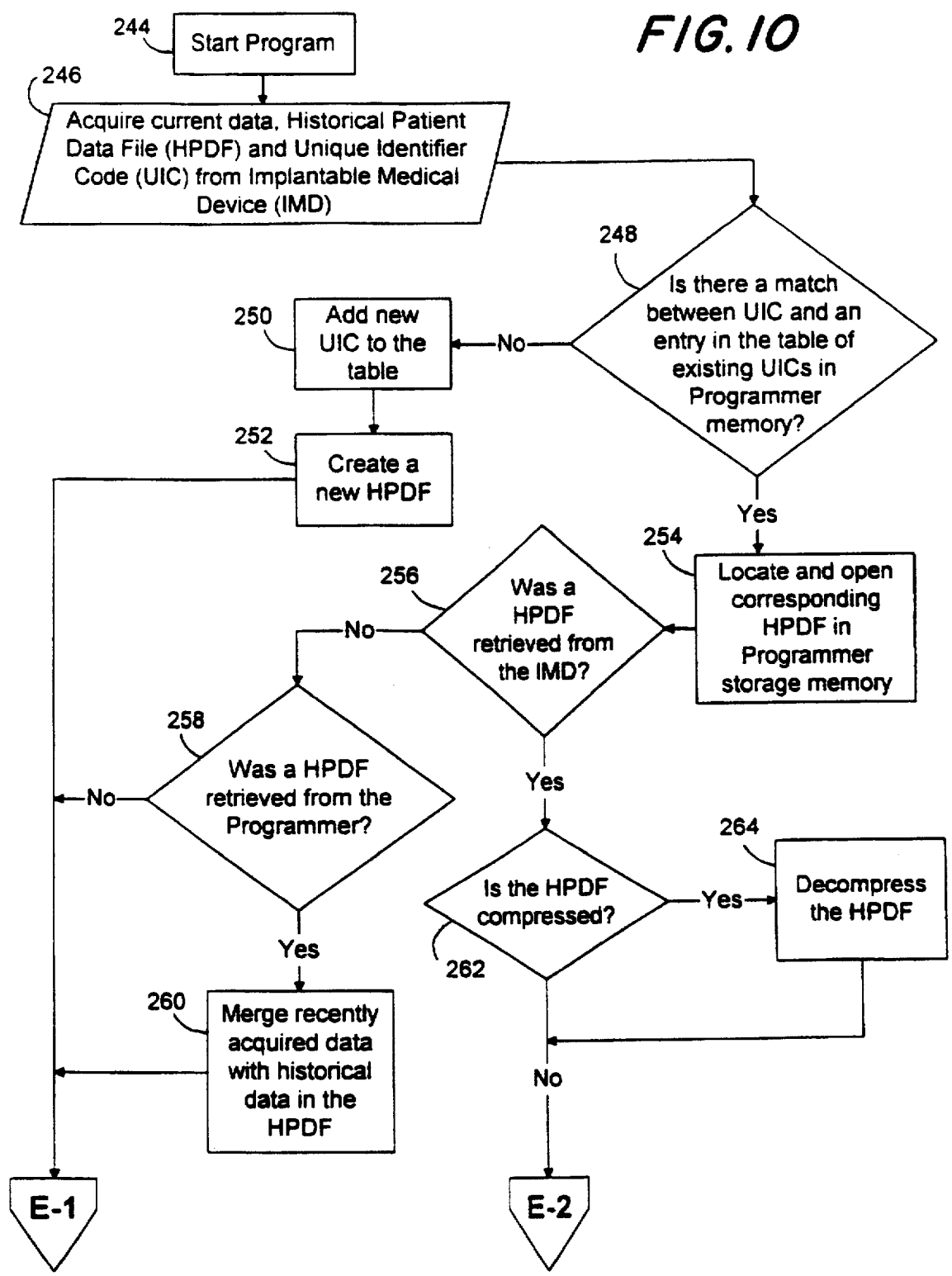
FIGS. 10–12 depict a logic flow diagram representative of a control program executed by the implantable device programmer, which is used to direct the operation of a third embodiment of the present invention in which the historical patient data file is stored in the implantable medical device memory and the programmer memory in accordance with the principles of the present invention.
Figure 11:
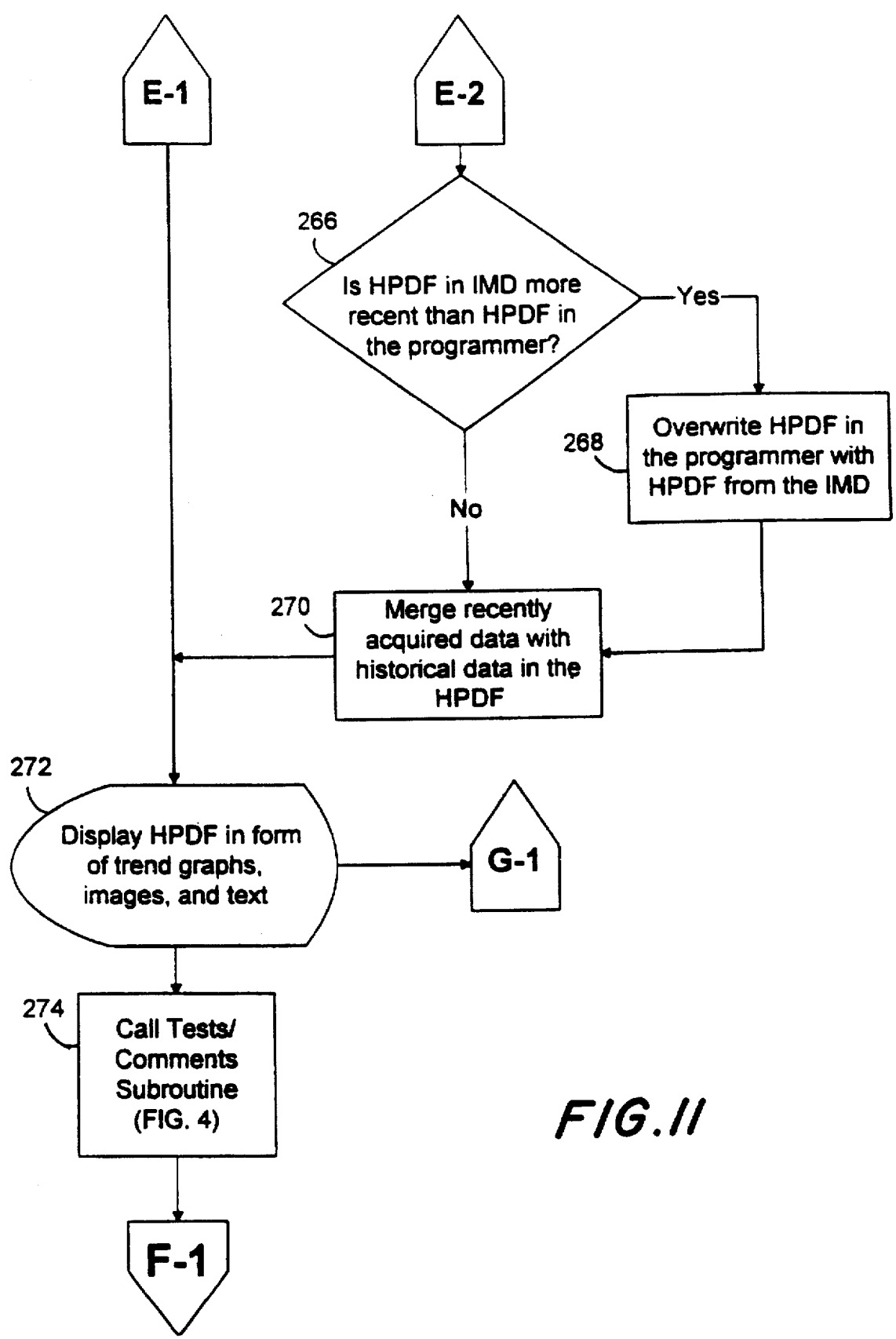
Figure 12:
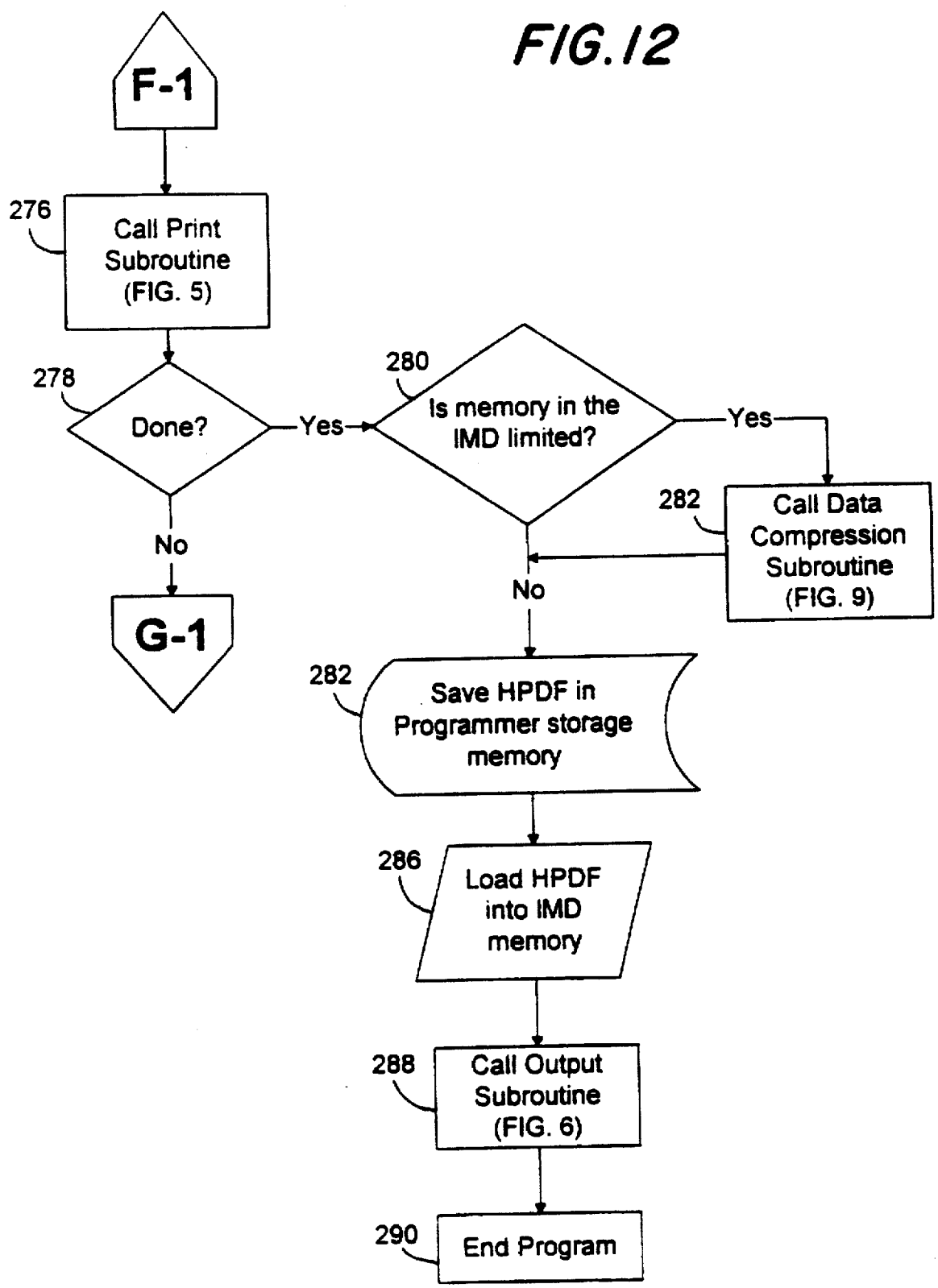

Referring now to FIGS. 10-12, a logic flow diagram representing a control program for the control unit 52 of FIG. 1 in accordance with a third embodiment of the present invention is described. In this embodiment, which combines the advantages of both of the previous embodiments, the historical patient data file is stored in the data memory area 38 (FIG. 1), and is also stored in the storage memory 56 (FIG. 1). Loss of data is known to occur in many forms of computer memory due to a variety of causes, such as strong magnetic fields, high amperage electrical pulses, static electricity, and physical shock. Thus, dual and redundant storage of medical data in the implantable medical device 30 and in the programmer 32 may be advantageous.

After the user begins the program at a step 244, at a step 246, the programmer control unit 52 (FIG. 1) acquires medical data from the implantable medical device 30 (FIG. 1) through telemetry. Medical data may include, but are not limited to, inter-visit data (if any are present), identification data (e.g., the UIC), and current physiologic and parametric data measured by the implantable medical device 30 (FIG. 1). At the step 246, the programmer control unit 52 (FIG. 1) also acquires the contents of the data memory area 38 (FIG. 1), where a historical patient data file may be stored. The medical data and the historical patient data file acquired at the step 246, may be acquired through telemetry locally by using the programmer telemetry head 60 (FIG. 1), or remotely through the data communication pathway 78 (FIG. 1) by using the modem 74 (FIG. 1) and the remote telemetry device 80 (FIG. 1). The recently acquired medical data and the historical patient data file are then temporarily stored in the programmer memory 54 (FIG. 1).

At a test 248 the programmer control unit 52 (FIG. 1) compares the acquired UIC against entries in a table of UICs stored in the storage memory 56 (FIG. 1). The programmer control unit 52 (FIG. 1) then determines whether the UIC acquired from the patient's implantable medical device 30 matches an entry in the table of UICs to ascertain whether the particular patient being examined has an existing historical patient data file in the programmer 32 (FIG. 1).

If at the test 248 the UIC acquired from patient's implantable medical device does not match any of the entries in the table of UICs, at a step 250 the programmer control unit 52 (FIG. 1) adds the new UIC to the table of UICs, and then creates a new historical patient data file at a step 252.

If at the test 248, the programmer control unit 52 (FIG. 1) determines that a match has been made between the UIC acquired from the patient's implantable medical device 30 (FIG. 1) and an entry in the table of UICs, at a step 254, the programmer control unit 52 (FIG. 1) locates the historical patient data file containing medical data from previous visits in the storage memory 56 (FIG. 1), and loads its contents into the programmer memory 54 (FIG. 1).

At a test 256, the programmer control unit 52 (FIG. 1) determines whether a historical patient data file was acquired from the data memory area 38 (FIG. 1) at the step 246. If no historical patient data file was acquired, the programmer control unit 52 (FIG. 1), at a test 258, determines whether a historical patient data file was retrieved from the storage memory 56 (FIG. 1) during the execution of step 254. If a historical patient data file was not retrieved, the program proceeds to the step 272. If a historical patient data file was retrieved, the programmer control unit 52 (FIG. 1) merges recently acquired medical data stored in programmer memory 54 (FIG. 1) into the historical patient data file retrieved from programmer storage memory 56 (FIG. 1) at a step 260. The program then proceeds to the step 72.

If at the test 256 the programmer control unit 52 (FIG. 1) determines that a historical patient data file was retrieved from the data memory area 38 (FIG. 1), at a test 262, the programmer control unit 52 (FIG. 1) determines if the retrieved historical patient data file is compressed. If the historical patient data file is not compressed, the program proceeds to a test 266. If the historical patient data file is compressed, at a step 264, the programmer control unit 52 (FIG. 1) decompresses the historical patient data file by one or more methods appropriate to each data format, as previously discussed in the description of the compression subroutine in connection with FIG. 9. The program then proceeds to the test 266.

At the test 266, the programmer control unit 52 (FIG. 1) determines if the historical patient data file acquired from the data memory area 38 (FIG. 1) is more recent then the historical patient data file stored in the storage memory 56 (FIG. 1). A disparity between the historical patient data file stored in the implantable medical device 30 and the historical patient data file stored in the programmer 32 may occur if the patient's last visit was with a different medical practitioner. For example, if the patient returned from an extended trip which entailed a visit with a medical practitioner who updated the historical patient data file in the data memory area 38 (FIG. 1), the historical patient data file in the current medical practitioner's programmer storage memory 56 (FIG. 1) would be outdated.

If at the test 266 the programmer control unit 52 (FIG. 1) determines that the historical patient data file acquired from the data memory area 38 (FIG. 1) is identical to the historical patient data file stored in the programmer storage memory 56 (FIG. 1), the program proceeds to a step 270. If the programmer control unit 52 (FIG. 1) determines that the historical patient data file acquired from the data memory area 38 (FIG. 1) is more recent than the historical patient data file stored in the programmer storage memory 56 (FIG. 1), at a step 268 the programmer control unit 52 (FIG. 1) copies the historical patient data file from the data memory area 38 (FIG. 1) to the programmer storage memory 56 (FIG. 1), and overwrites the outdated historical patient data file stored there. The program then proceeds to the step 270. At the step 270, the programmer control unit 52 (FIG. 1) merges the medical data acquired from the implantable medical device 30 (FIG. 1) at the step 246 into the historical patient data file stored in the programmer memory 54 (FIG. 1).

At a step 272, the historical patient data file stored in the programmer memory 54 (FIG. 1) is displayed to the user in form of physiologic and parametric data trend graphs, sampled waveforms, and text fields. At a step 274, the programmer control unit 52 (FIG. 1) calls the tests/comments subroutine (described above in connection with FIG. 4) which allows the user to perform additional tests on the patient and the implantable medical device 30 and add comments and test results to the historical patient data file. At a step 276, the programmer control unit 52 (FIG. 1) calls the print subroutine (described above in connection with FIG. 5). The print subroutine enables the user to print one or more portions of the historical patient data file stored in the programmer memory 54 (FIG. 1) on the printer 66 (FIG. 1).

The programmer control unit 52 (FIG. 1) then queries the user at a test 278 as to whether the tests/comments procedures are complete. If the procedures are not complete, the program returns to the step 272 where the updated historical patient data file is displayed. The user may then run more tests, and add more comments. If the procedures are complete, the programmer control unit 52 (FIG. 1) checks at a test 280 if the implantable medical device memory area 38 (FIG. 1) is of sufficient size to accommodate the storage of the decompressed updated historical patient data file. If the size of the data memory area 38 (FIG. 1) is insufficient, the programmer control unit 52 (FIG. 1) calls the compression subroutine (described above in connection with FIG. 9) at a step 282. The program then proceeds to a step 284. If the size of the data memory area 38 (FIG. 1) is sufficient, the program proceeds directly to the step 284.

At the step 284, the programmer control unit 52 (FIG. 1) saves the updated historical patient data file in the programmer storage memory 56 (FIG. 1). The programmer control unit 52 (FIG. 1) then loads the updated and compressed historical patient data file into the data memory area 38 (FIG. 1) at a step 286. The historical patient data file may be loaded into the data memory area 38 (FIG. 1) through telemetry locally, by using the programmer telemetry head 60 (FIG. 1), or remotely through the data communication pathway 78 (FIG. 1) by using the modem 74 (FIG. 1) and the remote telemetry device 80 (FIG. 1). The output subroutine (described above in connection with FIG. 6) is then called at a step 288 to allow the user to output the updated historical patient data file to a removable storage medium and to update the separate computer patient information file. The programmer control unit 52 (FIG. 1) then ends the program at a step 290, and returns to the initial display screen (not shown) on the display unit 58 (FIG. 1) where the user may begin another program.

Figure 13:
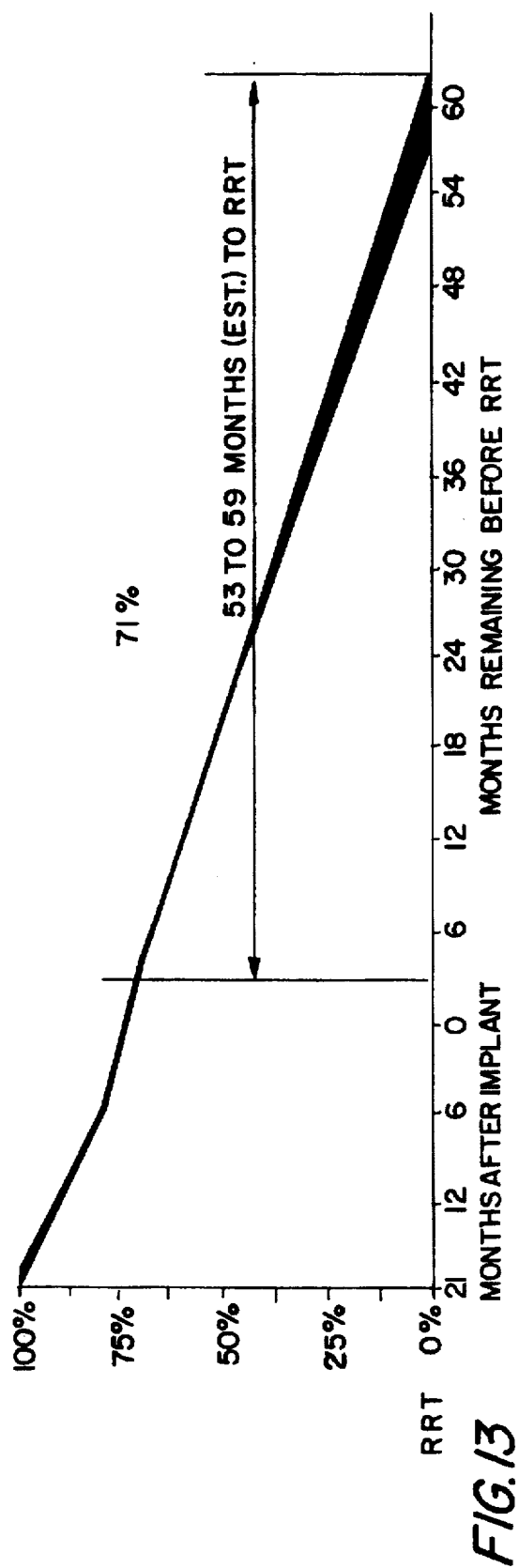
FIG. 13 is a trend graph of remaining implantable medical device battery life which is derived using data stored in the historical patient data file.

Referring now to FIGS. 13-16, some illustrative presentations of physiologic and parametric data that may be contained in a historical patient data file are shown. FIG. 13 shows the remaining battery life with estimated recommended replacement time (RRT) which is displayed on the display unit 58 (FIG. 1) as a function of percentage of battery 48 (FIG. 1) charge shown over expected time before its replacement. This is an example of parametric data which is likely to change from visit to visit and is important to the medical practitioner in deciding when to replace the battery 48 (FIG. 1).

Figure 14:
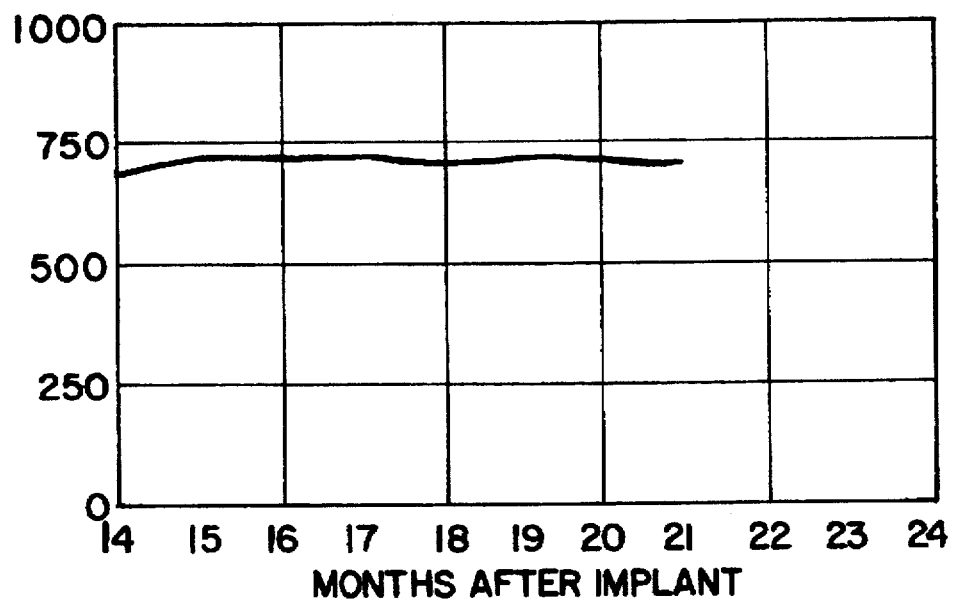
FIG. 14 is a trend graph of ventricular lead impedance which is derived using data stored in the historical patient data file.

FIG. 14 shows the ventricular lead impedance (in ohms) which is displayed on the display unit 58 (FIG. 1) as a function of months after implantation of the implantable medical device 30 (FIG. 1). This is an example of physiologic data which reflects the effectiveness of data acquisition and pulse delivery functions of the implantable medical device lead 44 (FIG. 1).

Figure 15:
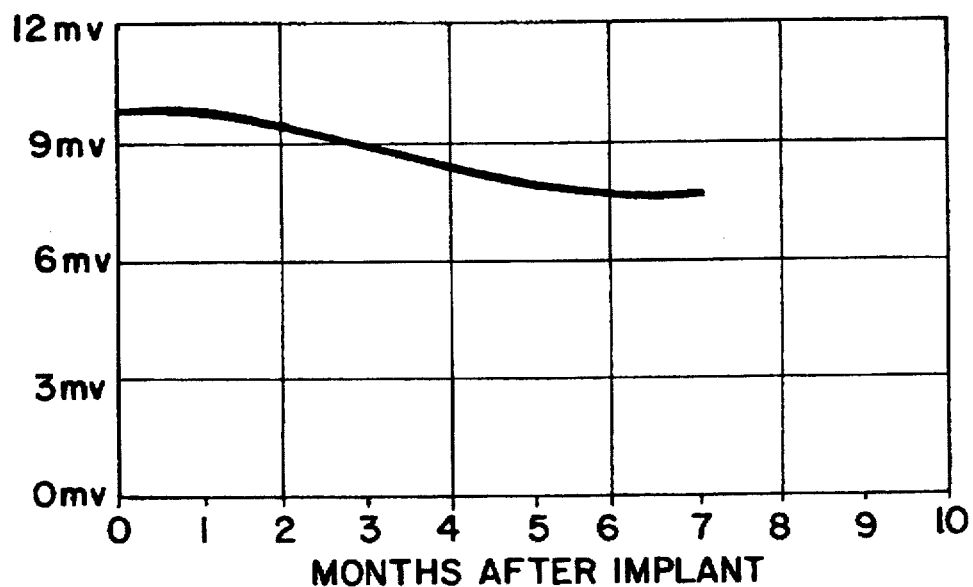
FIG. 15 is a trend graph of R-wave amplitude which is derived using data stored in the historical patient data file.

FIG. 15 shows R-wave amplitude (in millivolts) which is displayed on the display unit 58 (FIG. 1) as a function of months after the implantable medical device 30 (FIG. 1) is implanted. This is an example of physiologic data which represents average peak amplitudes of R-waves measured by the implantable medical device sensing circuit 42 (FIG. 1).

Figure 16:
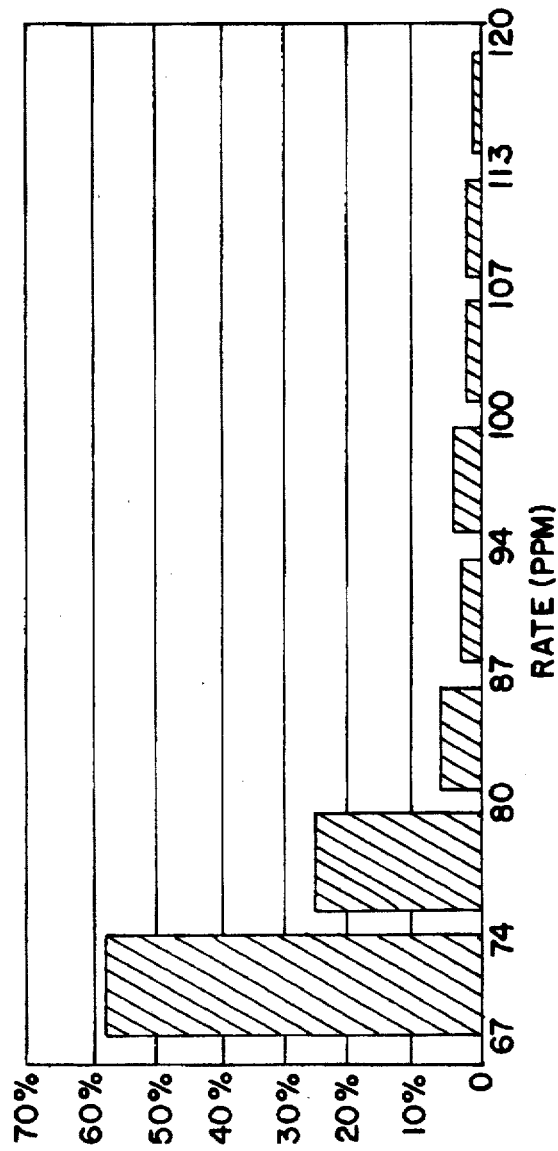
FIG. 16 is a histogram of sensor indicated rate which is derived using data stored in the historical patient data file.

Finally, FIG. 16 shows the sensor indicated rate which is displayed as a histogram showing a percent distribution for various heart rates of a patient during a pre-determined period of time as indicated by the implantable medical device sensing circuit 44 (FIG. 1). This information is useful to the medical practitioner since it gives an indication of the effectiveness of the therapy delivered by the implantable medical device 30.

Thus a system and method for acquiring medical data, integrating recently acquired medical data with previously acquired medical data, storing the integrated medical data, and displaying the integrated medical data to a medical practitioner in a convenient format appropriate for the type of data stored is provided. One skilled in the art will appreciate that the present invention can be practiced by other than the described embodiments, which are presented for purposes of illustration and not of limitation, and the present invention is limited only by the claims that follow.

What is claimed is:

1. A diagnostic system for use with a medical device implanted in a patient, wherein the medical device includes memory means, means for transmitting data from said memory means, and means for receiving data and storing said received data into said memory means, the system comprising:

telemetry means for receiving medical data transmitted by the medical device, the medical data including physiologic data pertaining to the patient's medical condition and parametric data pertaining to operating characteristics of the medical device;

long-term storage means for storing a historical patient data file containing medical data received from the medical device via the telemetry means;

control means for integrating medical data received from the medical device via the telemetry means during a current transmission into the historical patient data file stored in the long-term storage means, the historical patient data file thereafter containing medical data received during prior transmissions and the current transmission; and means for transmitting said integrated historical patient data file to the medical device.

2. The system of claim 1, wherein the telemetry means comprises:

remote telemetry means located in proximity to the patient for receiving medical data from the medical device and for sending medical data to the medical device;

modem means located in proximity to the diagnostic system for receiving medical data from the diagnostic system and for sending medical data to the diagnostic system; and data communication means coupling the modem means and the remote telemetry means for enabling transfer of medical data between the modem means and the remote telemetry means.

3. The system of claim 1, further comprising display means which, under control of the control means, displays medical data stored in the historical patient data file.

4. The system of claim 3, wherein the control means comprises means for causing the display means to display medical data in a format selected from the group consisting of a graphical data format, a form-based data format, and a textual data format.

5. The system of claim 4, wherein the graphical data format comprises waveforms and histograms.

6. The system of claim 1, wherein:

the system further comprises input means for receiving additional medical data including comments pertaining to the medical device and the patient's medical condition; and the control means comprises means for integrating the additional medical data into the historical patient data file.

7. The system of claim 1, wherein:

the system further comprises diagnostic means external to the medical device for acquiring additional medical data including physiologic data pertaining to the patient's medical condition and parametric data pertaining to operating characteristics of the medical device; and the control means comprises means for integrating the additional medical data into the historical patient data file.

8. The system of claim 1, wherein:

the system further comprises temporary storage means for temporarily storing the historical patient data file; and the control means further comprises means for causing transmission of the historical patient data file from the medical device to the temporary storage means via the telemetry means.

9. The system of claim 8, wherein the system further comprises input means and the means for causing transmission causes transmission in response to a command received via the input means.

10. The system of claim 1, wherein the long-term storage means further comprises external memory means for storing a copy of the historical patient data file.

11. The system of claim 10, wherein the control means further comprises means for determining whether the historical patient data file stored in the medical device memory means and the copy of the historical patient data file stored in the external memory means are consistent.

12. The system of claim 11, wherein the control means further comprises means for replacing the copy of the historical patient data file stored in the external memory means with the historical patient data file stored in the medical device memory means when the copy of the historical patient data file stored in the external memory means and the historical patient data file stored in the medical device memory means are inconsistent.

13. The system of claim 1, wherein the control means comprises means for compressing medical data stored the historical patient data file.

14. The system of claim 1, wherein the control means comprises:

means for determining whether the historical patient data file exists in the long-term storage means; and means for creating the historical patient data file in the long-term storage means when the means for determining determines that the historical patient data file does not exist in the long-term storage means.

15. The system of claim 1, wherein the long-term storage means stores a plurality of historical patient data files, each historical patient data file being identifiable by a unique identifier.

16. The system of claim 16, wherein the control means comprises:

means for receiving identification data from the medical device via the telemetry means; and means for selecting a historical patient data file from the plurality of historical patient data files by comparing the received identification data to the unique identifier associated with each historical patient data file.

17. A programming system for communicating with an implantable medical device which is responsive to control signals, the implantable medical device including a memory circuit, data acquisition circuitry for acquiring medical data, a telemetry circuit for receiving the control signals, for transmitting the medical data acquired by the data acquisition circuitry, and for receiving data and storing the received data into the memory circuit, the programming system comprising:

a telemetry head for transmitting the control signals to and receiving the medical data from the implantable medical device via the telemetry circuit;

a long-term storage device for storing a historical patient data file containing the medical data received from the implantable medical device;

an input device;

a control unit for interpreting commands received via the input device, for causing the telemetry head to transmit the control signals to the implantable medical device, the control signals being representative of commands received via the input device, for integrating the medical data received via the telemetry head during a current transmission from the implantable medical device into the historical patient data file, the historical patient data file thereafter containing medical data received during prior transmissions from the implantable medical device and the current transmission, and for causing the telemetry head to transmit the integrated historical patient data file to the implantable medical device; and a display unit for displaying the medical data stored in the historical patient data file.

18. The system of claim 17, further comprising:

a remote telemetry device located in proximity to the patient comprising:

a data communication device; and a telemetry head for receiving medical data from, and sending medical data to the medical device via the telemetry circuit;

a modem coupled to the diagnostic system for receiving medical data from the diagnostic system and for sending medical data to the diagnostic system; and wherein the modem and the remote telemetry device are coupled by a data communication pathway for transfer of medical data between the modem and the remote telemetry device.

19. The system of claim 17, wherein the medical data comprises physiologic data pertaining to a patient's medical condition and parametric data pertaining to operational characteristics of the implantable medical device.

20. The system of claim 17, wherein the display unit displays the medical data in a format selected from the group consisting of a graphical data format, a form-based data format, and a textual data format.

21. The system of claim 17, wherein the graphical data format comprises waveforms and histograms.

22. The system of claim 17, wherein:

the input device receives additional medical data including comments pertaining to the implantable medical device and a patient's medical condition; and the control unit integrates the additional medical data into the historical patient data file.

23. The system of claim 17, wherein:

the system further comprises:

a plurality of leads externally coupled to the programming system for acquiring surface medical data including physiologic data pertaining to the patient's medical condition and parametric data pertaining to operating characteristics of the medical device in an analog format; and a diagnostic circuit for converting surface medical data received from the plurality of external leads into digital form suitable for integration with the historical patient data file; and the control unit integrates surface medical data into the historical patient data file.

24. The system of claim 17, wherein:

the system further comprises a temporary storage device for temporarily storing the historical patient data file; and the control unit causes transmission of the historical patient data file from the implantable medical device to the temporary storage device via the telemetry head.

25. The system of claim 24, wherein the control unit causes transmission in response to a request received via the input device.

26. The system of claim 17, wherein the long-term storage device further comprises an external memory device which stores a copy of the historical patient data file.

27. The system of claim 26, wherein the control unit determines whether the historical patient data file stored in the medical device memory circuit and the copy of the historical patient data file stored in the external memory device are consistent.

28. The system of claim 27, wherein the control unit replaces the copy of the historical patient data file stored in the external memory device with the historical patient data file stored in the medical device memory circuit when the copy of the historical patient data file stored in the external memory device and the historical patient data file stored in the medical device memory circuit are inconsistent.

29. The system of claim 17, wherein the control unit compresses medical data stored in the historical patient data file.

30. The system of claim 17, wherein the control unit:

determines whether the historical patient data file exists in the long-term storage device; and creates the historical patient data file in the long-term storage device when the historical patient data file does not exist in the long-term storage device.

31. The system of claim 17, wherein the long-term storage device stores a plurality of historical patient data files, each historical patient data file being identifiable by a unique identifier.

32. The system of claim 31, wherein the control unit:

receives identification data from the medical device via the telemetry head; and selects a historical patient data file from the plurality of historical patient data files by comparing the received identification data to the unique identifier associated with each historical patient data file.

33. A diagnostic method for use with a medical device implanted in a patient, the method comprising the steps of:

telemetrically receiving medical data transmitted by the medical device, the medical data including physiologic data pertaining to the patient's medical condition and parametric data pertaining to operating characteristics of the medical device storing in a long-term storage device a historical patient data file containing medical data telemetrically received from the medical device;

integrating medical data telemetrically received from the medical device during a current transmission into the historical patient data file stored in the long-term storage device, the historical patient data file thereafter containing medical data received during prior transmissions and the current transmission; and telemetrically transmitting the integrated historical patient data file to the medical device for storage in a medical device memory circuit disposed within the medical device.

34. The method of claim 33, further comprising the step of displaying medical data stored in the historical patient data file.

35. The method of claim 34, wherein the displaying step comprises displaying medical data in a format selected from the group consisting of a graphical data format, a form-based data format, and a textual data format.

36. The method of claim 35, wherein the graphical data format comprises waveforms and histograms.

37. The method of claim 33, further comprising the steps of:

receiving via an input device additional medical data including comments pertaining to the medical device and the patient's medical condition; and integrating the additional medical data into the historical patient data file.

38. The method of claim 33, further comprising the steps of:

acquiring via a plurality of external leads surface medical data including physiologic data pertaining to the patient's medical condition and parametric data pertaining to operating characteristics of the medical device; and converting surface medical data received from the plurality of external leads into digital form suitable for integration with the historical patient data file; and integrating the surface medical data into the historical patient data file.

39. The method of claim 33, further comprising the step of telemetrically transmitting the historical patient data file from the medical device to a temporary storage device.

40. The method of claim 39, wherein the historical patient data file is telemetrically transmitted from the medical device to the temporary storage device in response to a command received from an input device.

41. The method of claim 33, wherein the storing step further comprises the step of storing a copy of the historical patient data file in an external storage device.

42. The method of claim 41, further comprising the step of determining whether the historical patient data file stored in the medical device memory circuit and the copy of the historical patient data file stored in the external memory device are consistent.

43. The method of claim 42, further comprising the step of replacing the copy of the historical patient data file stored in the external memory device with the historical patient data file stored in the medical device memory circuit when the copy of the historical patient data file stored in the external memory device and the historical patient data file stored in the medical device memory circuit are inconsistent.

44. The method of claim 33, further comprising the step of compressing medical data stored in the historical patient data file.

45. The method of claim 33, further comprising the steps of:

determining whether the historical patient data file exists in the long-term storage device; and creating the historical patient data file in the long-term storage device when the historical patient data file does not exist in the long-term storage means.

46. The method of claim 33, wherein the storing step comprises the step of storing a plurality of historical patient data files, each historical patient data file being identifiable by a unique identifier.

47. The method of claim 46, further comprising the steps of:

telemetrically receiving identification data from the medical device; and selecting a historical patient data file from the plurality of historical patient data files by comparing the received identification data to the unique identifier associated with each historical patient data file.

48. A diagnostic system for use with a medical device implanted in a patient, wherein the medical device includes memory means, wherein a patient data file is stored in the memory means, means for transmitting the patient data file from said memory means, and means for receiving data and storing said received data into said memory means, the system comprising:

telemetry means for receiving the patient data file data transmitted by the medical device;

long-term storage means for storing a historical patient data file;

control means for integrating the patient data file received from the medical device via the telemetry means during a current transmission into the historical patient data file stored in the long-term storage means; and means for transmitting said integrated historical patient data file to the medical device.

49. A programming system for communicating with an implantable medical device which is responsive to control signals, the implantable medical device including a memory circuit containing a patient data file and a telemetry circuit for transmitting the patient data file and for receiving data and storing the received data into the memory circuit, the programming system comprising:

a telemetry system for transmitting and receiving data from the implantable medical device via the telemetry circuit;

a long-term storage device for storing a historical patient data file;

an input device; and a control unit for interpreting commands received via the input device, for causing the telemetry system to receive the patient data file transmitted by the implantable medical device, for integrating the received patient data file into the historical patient data file, and for causing the telemetry system to transmit the integrated historical patient data file to the implantable medical device.

50. The system of claim 49, wherein the programming system further comprises an input device which receives additional medical data including comments pertaining to the implantable medical device and a patient's medical condition; and the control unit integrates the additional medical data into the historical patient data file.

51. The system of claim 49, wherein the control unit determines whether the patient data file stored in the medical device memory circuit and the copy of the historical patient data file stored in the long-term storage device are consistent.

52. The system of claim 51, wherein the control unit replaces the copy of the historical patient data file stored in the long-term storage device with the patient data file stored in the medical device memory circuit when the copy of the historical patient data file stored in the long-term storage device and the patient data file stored in the medical device memory circuit are inconsistent.

53. The system of claim 49, wherein the control unit:
   determines whether the historical patient data file exists in the long-term storage device; and
   creates the historical patient data file in the long-term storage device when the historical patient data file does not exist in the long-term storage device.

54. The system of claim 49, wherein the long-term storage device stores a plurality of historical patient data files, each historical patient data file being identifiable by a unique identifier.

55. The system of claim 54, wherein the control unit:
   receives identification data from the medical device via the telemetry system; and
   selects a historical patient data file from the plurality of historical patient data files by comparing the received identification data to the unique identifier associated with each historical patient data file.

56. The system of claim 49, wherein the control unit:
   determines whether the historical patient data file exists in the long-term storage device; and
   updates the historical patient data file in the long-term storage device when the historical patient data file does exist in the long-term storage device.

* * * * *